US012635709B2

(12) United States Patent
Lihme et al.

(10) Patent No.: US 12,635,709 B2
(45) Date of Patent: *May 26, 2026

(54) METHOD FOR SEPARATION OF PROTEINS NATURALLY OCCURRING IN MAMMALIAN MILK

(71) Applicant: Lihme Protein Solutions ApS, Farum (DK)

(72) Inventors: Allan Otto Fog Lihme, Farum (DK); Marie Bendix Hansen, Frederiksberg (DK)

(73) Assignee: Lihme Protein Solutions ApS, Farum (DK)

( * ) Notice: Subject to any disclaimer, the term of this patent is extended or adjusted under 35 U.S.C. 154(b) by 1227 days.

This patent is subject to a terminal disclaimer.

(21) Appl. No.: 16/982,088

(22) PCT Filed: Apr. 5, 2019

(86) PCT No.: PCT/EP2019/058683
§ 371 (c)(1),
(2) Date: Sep. 18, 2020

(87) PCT Pub. No.: WO2019/197292
PCT Pub. Date: Oct. 17, 2019

(65) Prior Publication Data
US 2021/0106025 A1 Apr. 15, 2021

(30) Foreign Application Priority Data
Apr. 9, 2018 (DK) ............................ PA 2018 70210

(51) Int. Cl.
| | |
|---|---|
| *A61K 39/395* | (2006.01) |
| *A23C 21/10* | (2006.01) |
| *A23J 1/20* | (2006.01) |
| *A23J 3/08* | (2006.01) |
| *C07K 1/32* | (2006.01) |

(52) U.S. Cl.
CPC ................. *A23J 1/20* (2013.01); *A23C 21/10* (2013.01); *A23J 3/08* (2013.01); *C07K 1/32* (2013.01)

(58) Field of Classification Search
None
See application file for complete search history.

(56) References Cited

U.S. PATENT DOCUMENTS

| | | | | |
|---|---|---|---|---|
| 855,870 | A | 6/1907 | Wittkowsky | |
| 2,588,392 | A | 3/1952 | Julian et al. | |
| 7,368,141 | B2 * | 5/2008 | Lihme ..................... | A23J 1/202 426/531 |
| 11,623,942 | B2 * | 4/2023 | Lihme ..................... | A23J 1/008 530/420 |
| 2014/0322548 | A1 | 10/2014 | Boldizsar | |

FOREIGN PATENT DOCUMENTS

| | | |
|---|---|---|
| CN | 103289967 | 9/2013 |
| WO | WO2005056808 | 6/2005 |
| WO | WO2018082759 | 5/2018 |
| WO | WO2018162557 | 9/2018 |

OTHER PUBLICATIONS

Keen, C. et al., "Superoxide dismutase isoenzymes in bovine and human milk", Biological Trace Element Research, vol. 2(3), pp. 221-227, XP002784829, (Sep. 1980).
Coradin, T. et al., "Interactions of amino-containing peptides with sodium silicate and colloidal silica: a biomimetic approach of silicification", American Chemical Society, vol. 18(6), pp. 2331-2336, XP003002129, (2002).
Ghose, S. et al., "Preparative protein purification on underivatized silica", Biotechnology and Bioengineering, vol. 87 (3), pp. 413-423, XP055506626, (Aug. 2004).
WPI, Week 201415, Clarivate Analytics, pp. 1-2, XP002784830, (2017).

* cited by examiner

*Primary Examiner* — Yunsoo Kim
(74) *Attorney, Agent, or Firm* — McHale & Slavin, P.A.

(57) ABSTRACT

The present invention relates to method for purifying proteins naturally occurring in mammalian milk from aqueous protein solution using water-soluble silicate. The silicates form an insoluble precipitate of a silicate-protein complex from which the proteins can be isolated.

21 Claims, 9 Drawing Sheets

Figure 1A:
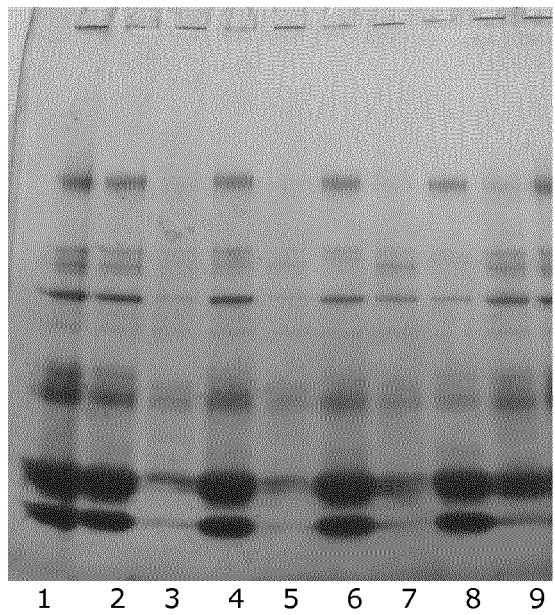

IgG
LF
BSA

GMP
beta-lg
alpha-la 1   2   3   4   5   6   7   8   9

IgG
LF
BSA

GMP
beta-lg
alpha-la 10  11  12  13  14  15  16  17  18

IgG

LF
BSA beta-lg
alpha-la 1   2   3

IgG
LF
BSA beta-lg
alpha-la 1  2  3  4  5

IgG
LF
BSA beta-lg
alpha-la 1  2  3  4  5  6

IgG
LF
BSA beta-lg
alpha-la 1  2  3  4  5  6  7

IgG

BSA beta-Ig
alpha-la 1   2   3   4   5

IgG
LF
BSA

GMP
beta-Ig
alpha-la 1   2   3   4   5

IgG
LF
BSA

GMP
beta-lg
alpha-la 6  7  8

IgG
LF
BSA

GMP
beta-lg
alpha-la 1  2  3  4  5  6

IgG

LF
BSA beta-Ig
alpha-la 1  2  3  4

IgG

LF
BSA beta-Ig
alpha-la 5  6  7  8

IgG

LF

BSA beta-Ig alpha-la 1    2    3    4        5    6    7    8

IgG

LF

BSA beta-Ig alpha-la 1    2    3    4    5

IgG
LF
BSA beta-lg
alpha-la 1   2   3     4   5   6

IgG
LF
BSA beta-lg
alpha-la 7   8   9   10   11 12 13

IgG

LF
BSA beta-lg
alpha-la 1   2   3   4   5   6   7   8

METHOD FOR SEPARATION OF PROTEINS NATURALLY OCCURRING IN MAMMALIAN MILK

CROSS REFERENCE TO RELATED APPLICATIONS

This is a national stage filing in accordance with 35 U.S.C. § 371 of PCT/EP2019/058683, filed Apr. 5, 2019, which claims the benefit of the priority of Denmark Patent Application No. PA 2018 70210, filed Apr. 9, 2018, the contents of each are incorporated herein by reference.

FIELD OF THE INVENTION

The present invention relates to methods for purifying proteins naturally occurring in milk using soluble silicates, and products such as silicate-protein complexes and proteins separated by such methods.

BACKGROUND OF THE INVENTION

Techniques for industrial scale isolation of proteins from complex liquid raw materials have been a target of constant development for more than a century. Very many different methods based on various physico-chemical parameters have been described in the prior art but only few have found industrial applicability.

Purified proteins may be of value in widely different areas such as pharmaceutical, food, feed and technical applications and for each specific application there will be different target specifications for the purity and functionality of the protein. Likewise, the market value for a certain protein depends on the type of application. Thus, proteins intended for pharmaceutical applications have a much higher market value than proteins intended for food or feed applications. It is therefore crucial that any methodology, and its associated process cost, chosen for the isolation of a protein is carefully balanced against the value of the protein.

Precipitation of proteins from aqueous solutions is widely used for large scale separation. Proteins may be precipitated by adding various agents such as organic solvents, lyotropic salts (such as ammonium sulfate) or polymers of different kind. Many food proteins are isolated from plant extracts (such as aqueous extracts of soy beans and peas) by so-called isoelectric precipitation which is based on the natural tendency of some proteins to become insoluble at pH values where the protein surface exhibits a near zero net charge. Isoelectric precipitation of proteins is generally a very low-cost operation. However, the method has limitations due to a rather low selectivity, co-precipitation of other unwanted substances and a narrow window of operation. A major drawback of the isoelectric precipitation method is that it is difficult to remove the co-precipitated impurities by washing of the precipitated proteins because any change of the conditions (such as pH, temperature and ionic strength) may lead to solubilization and loss of the protein. Another major drawback of the isoelectric precipitation method is that only certain proteins will precipitate, leaving significant amounts of otherwise valuable proteins in the mother liquid and thereby lead to economic losses and environmental burdens from the associated waste water. Precipitation of proteins by the addition of chemical substances such as organic solvents, lyotropic salts and polymers is not generally applied for the industrial separation of food and feed grade proteins due to the high costs associated with the chemicals, the high costs of chemicals recycling and treatment of waste water and the need to completely remove these chemicals from the product after the precipitation process.

Precipitation of proteins from aqueous solutions may also be performed by the application of heat, such as heating to 60-100 degrees Celsius or 110-130 degrees Celsius under increased pressure, or even by heating combined with adjustment of pH to highly acidic pH values. Such processes are industrially applied, for example in order to precipitate potato proteins from potato fruit juice produced as a side-stream in the potato starch manufacturing industry. Such processes may be highly efficient; however, the proteins will be completely denatured by the process conditions. Typically, such treated proteins will be largely insoluble and any biological activity and functional characteristics will be lost.

Membrane filtration is another widely and industrially used method for the isolation and concentration of proteins from complex mixtures. The fundamental separation principle is based on the passing of the liquid through semi-permeable membranes allowing only the passage of molecules smaller than the size of the porous structure of the membrane. Thus, membrane filtration separates molecules largely on the basis of their size and the availability of membranes with different pore sizes enables the separation of molecules and particles of varying size ranges. However, in order to achieve an efficient separation, the molecules to be separated must have very different sizes (such as at least 10 times different size). Molecules being closer in size will only be partially separated which may be detrimental to the product yield and thereby the economy of the separation process. Thus, membrane filtration, such as ultrafiltration and microfiltration, is intensively used in the dairy industry to separate proteins from milk and whey. Hereby highly purified protein mixtures devoid of lactose, milk fat and minerals may be produced at very large scale. Examples of such membrane produced protein products are WPC 80 and WPI (Whey Protein Concentrate and Whey Protein Isolate respectively) which are mixtures of the dominant whey proteins e.g. beta-lactoglobulin, alpha-lactalbumin, immunoglobulins and lactoferrin with a very low content of lactose, minerals and lipids. On the other hand, and due to the comparable size of the proteins, membrane filtration is generally not industrially used for the separation of these protein mixtures into their single protein components.

Solid phase adsorption (adsorption chromatography) is based on the reversible interaction of molecules in a solution with the surface structures of an insoluble adsorbent material. Silica gels, in the form of silicon dioxide beads or coarse granules, constitute a specific type of solid phase adsorbents that may be produced with varying pore size and available surface area. Agarose beads and synthetic polymer beads constitute other groups of solid phase adsorbents with different characteristics for different protein separation tasks. The surface of the insoluble adsorbent material may be chemically derivatized to facilitate interaction with molecules of widely different nature and can be designed to achieve highly selective separation of even closely related molecules. Thus, solid phase adsorption is widely applied in the manufacture of proteins for pharmaceutical applications.

The use of a solid phase adsorbent for isolation of proteins typically comprise the following steps:

Equilibration of the solid phase adsorbent, which involves washing of the adsorbent with buffers that conditions the adsorbent surface to the pH and ionic strength suitable for binding of the target molecule

Conditioning of the liquid raw material, which typically involves adjustment of pH and ionic strength suitable for binding of the target molecule to the sloid phase adsorbent Contacting the solid phase adsorbent with the liquid raw material for a time span sufficient to ensure diffusion of the target molecule into the porous structures of the adsorbent and allow a binding equilibrium to take place Washing of the solid phase adsorbent with buffers to remove unwanted impurities Elution of the target molecule by incubation with buffers changing the conditions such that the bound molecules are released and diffuse out of the adsorbent for collection.

Cleaning of the adsorbent to ensure complete removal of all bound substances prior to reusing the adsorbent. This is typically performed with highly caustic or highly acidic chemical agents comprising detergents and other aggressive cleaning agents. This step is important to avoid carry-over of substances from cycle to cycle and to avoid, or delay, a gradual inactivation of the adsorbent surface by irreversible fouling of very hard binding substances.

Re-equillibration of the adsorbent to make it ready for a repeated cycle of target molecule binding.

Due to the high selectivity of solid phase adsorption this methodology has attracted much attention for separation tasks requiring high product purity. However, the cost of the adsorbents, the time-consuming cycling between binding and release of target molecules and the high water and chemicals consumption for washing, cleaning and regeneration of the adsorbents all adds to the high cost of using this separation technology. Therefore, solid phase separation is only rarely used for the isolation of food and feed grade proteins.

Milk is a very complex material and industrial processes use milk to produce casein, whey, lactose, condensed milk, powdered milk, and many other food-additives and industrial products. Milk comprises a mixture of components, such as proteins, minerals, fat, sugars, salts, and vitamins. In particular, the proteins in milk, which are mainly found as casein proteins or whey proteins, have gained increasingly attention over the years.

The reason for this increased interest lies in the diversity of milk proteins and because each protein has unique attributes to nutritional, biological, functional and food ingredient applications.

Furthermore, these proteins constitute, together with e.g. peptides and enzymes in milk, a major and important health and nutritional role in humans and animals.

To achieve highest possible potential of proteins and to explore or exploit the potentially functional and bioactive properties of proteins, and especially whey proteins, it is important to isolate native whey proteins by a procedure that avoids possible denaturing conditions.

Except from casein products, like cheese, the most commonly produced milk protein products are Whey Protein Concentrates (WPC) and Whey Protein Isolates (WPI). These WPC7 and WPI products are standard products obtained from whey through various separation techniques, such as membrane filtration techniques as well as ion exchange adsorption procedures. Further fractionation of the WPC proteins or the WPI proteins into individual protein fractions, such as a beta-lactoglobulin fraction, an alpha-lactalbumin fraction, an immunoglobulin fraction, a lactoperoxidase fraction, and a lactoferrin fraction, is made possible by using a chromatographic support, however, this methodology is often too laborious and expensive to provide products with a cost relevant for use in non-pharmaceutical, such as food and dietary, applications.

Whey, the liquid residue of cheese, casein and yoghurt production, is one of the biggest reservoirs of food protein available today. World whey output at approximately 180 million tonnes in 2013 contains some 1.5 million tonnes of increasingly high-value protein and 8.6 million tonnes of lactose, a very important source of carbohydrate for the world. Whey comprises 80-90% of the total volume of milk entering the process and contains about 50% of the nutrients in the original milk: soluble protein, lactose, vitamins and minerals.

Whey as a by-product from the manufacture of hard, semi-hard or soft cheese and rennet casein is known as sweet whey and has a pH of 5.9-6.6. Manufacture of mineral-acid precipitated casein yields acid whey with a pH of 4.3-4.6.

Table 1 shows the approximate composition figures for sweet whey from cheese manufacture and acid whey from casein manufacture.

TABLE 1

| Constituent | Sweet whey | Acid whey |
|---|---|---|
| | % | % |
| Total solids | 6.0 | 6.4 |
| Water | 94 | 93.6 |
| Fat | 0.05 | 0.05 |
| True protein | 0.60 | 0.60 |
| NPN (non-protein nitrogen) | 0.20 | 0.20 |
| Lactose | 4.5 | 4.6 |
| Ash (minerals) | 0.5 | 0.8 |
| Calcium | 0.035 | 0.12 |
| Phosphorus | 0.040 | 0.065 |
| Sodium | 0.045 | 0.050 |
| Potassium | 0.14 | 0.16 |
| Chloride | 0.09 | 0.11 |
| Lactic acid | 0.05 | 0.05 |

Acid whey from cottage cheese and casein production is difficult to process and to dry due to its high lactic acid and calcium content. It has a tendency to be fouling during membrane filtration and agglomerates and forms lumps in spray dryers.

An alternative method to produce whey uses microfiltration with a skimmed milk feed instead of coagulating the casein in a cheese process or by acidification. This microfiltration process produce concentrated micellar casein in the retentate and native whey proteins in the permeate. The casein in the concentrate is in its native micellar form, unlike acid casein, which is denatured when precipitated from milk using acids. Native whey proteins are a potential alternative to whey protein concentrates obtained from cheese making with the added benefits of not being denatured or containing any residual products, such as glycomacropeptide, from cheesemaking and a lower fat content.

Infant formulas to be used as substitutes for human milk for new born children are often manufactured from cow's milk including the caseins and whey proteins present in cow's milk. Historically the cow's milk proteins have been separated and concentrated from unfractionated raw materials giving rise to infant formulas having a protein composition close to the composition found in cow's milk. However, there are significant differences in the concentration of individual proteins in human milk and cow's milk respectively. For example, the protein beta-lactoglobulin is the most abundant protein found in whey derived from cow's milk while no such protein is present in human milk. In contrast, human milk contains high concentrations of alpha-lactalbumin and lactoferrin, while these proteins are present in cow's milk only at relatively low concentrations. Recently there have been several attempts to isolate the individual proteins from cow's milk in order to recombine them in infant formula products that resemble the human milk more closely than what has hitherto been the case. Such protein isolation processes need to be highly selective, being mild to the proteins, giving high product yields and be very economical in use in order to enable a general commercial distribution. However, it has proven difficult to achieve all of these targets with the prior art processes that typically lack in selectivity (such as membrane processes), are far too expensive to be commercialized (such as chromatographic separation) or are destructive to the proteins (such as precipitation by heat).

Lactoferrin is one of the principal proteins responsible for providing protection to infant mammals before their immune systems begin to function. It is a minor protein in cow's milk (100-300 mg/L) and is extracted from skim milk or whey through protein separation. As an iron-binding glycoprotein of the transferrin family, Lactoferrin is found in high concentrations in mother's milk. It is used throughout the US, Europe and Asia as a nutritional supplement or as an additive to infant formula.

Alpha-lactalbumin is a major whey protein containing a naturally high content of all essential and branched-chain amino acids (BCAA), making it a unique protein source for food and dietary applications. The most significant amino acids contained in alpha-lactalbumin are tryptophan and cysteine, together with the BCAAs; leucine, isoleucine and valine. Due to the high content of branched-chain amino acids (BCAA, ~26%), and especially leucine, alpha-lactalbumin effectively supports and stimulates muscle protein synthesis, making it the ideal protein source for improving muscle health and help prevent sarcopenia during ageing. Alpha-lactalbumin is also one of the food proteins with the highest content of the amino acid tryptophan. Tryptophan (Trp) is an essential amino acid that has to be obtained from the diet and cannot itself be synthesised in the body. Tryptophan is the precursor of serotonin, which is a neurotransmitter and also functions as the precursor to melatonin (hormone involved in the sleep-wake cycle). Serotonin exerts multiple effects and is implicated in the control of the appetite, mood, sleep regulation, cognitive performance and the ability to cope with stress.vAlpha-lactalbumin offers a natural way to formulate foods tailored to boost the body's serotonin production with various effects related to healthy weight and natural well-being.

β-lactoglobulin is one of major whey proteins in bovine milk, constituting approximately 50% of total whey protein. Bovine β-lactoglobulin contains 162 amino acids (MW 18.4 kDa) and its isoelectric point is 5.3. The protein is known for its high value as food ingredients and its functional properties, especially as a highly gelling agent.

However, one of the most important allergens in milk is β-lactoglobulin (β-lg) to which about 82% of milk allergic patients are sensitive. Therefore, for the manufacture of hypoallergenic milk or whey products, it will be advantageous to selectively and efficiently remove the β-lg without harming the quality and composition of the remaining proteins.

Casein macropeptide (CMP) is a highly heterogeneous peptide due to a variety of glycosylation patterns and different extents of glycosylations by galactosamine, galactose and o-sialic acid. For this reason, CMP does not have a single charge but in reality a distribution of charges exists.

CMP is a unique, naturally occurring peptide that contains no Phenylalanine (Phe). CMP is e.g. formed during cheese-making when chymosin specifically cleaves K-casein between the 105 to 106 amino acid residues. Para-K-casein (residues 1 to 105) coagulates, forming cheese curd, while CMP (residues 106 to 169) remains in the whey. CMP is the $3^{rd}$ most abundant protein in sweet whey, after β-lactoglobulin (BLG) and α-lactalbumin (ALA), and makes up 15% to 25% of the total whey protein. CMP is present at a concentration of 1.2 to 1.5 g/L in whey. The lack of Phe makes CMP an interesting protein source for persons suffering from phenylketonuria (PKU).

Milk and milk products contain growth factors such as insulin-like IGF-I, IGF-II, epidermal growth factor EGF, transforming growth factors TGF-31 and TGF-32, the basic fibroblast growth factor bFGF and the platelet-derived growth factor PDGF that can have a beneficial activity. These growth factors are present in very low concentrations in the milk, which is why they are sometimes referred to as micronutrients. They can be characterised by their isoelectric point, which is relatively high compared to other milk proteins and their molecular weight. TGF-β is a multifunctional protein found in all mammalian tissues. Currently, five forms of TGF-β are known, β1 to β5. It has been implicated in the development, differentiation and growth of tissue and the control of immune system function and carcinogenesis. TGF-β can be isolated from natural sources (e.g. blood platelets), mammalian milk or colostrum or can be produced by recombinant cells. IGF-1, an anabolic, i.e. growth promoting, growth factor, is a small protein (molecular weight about 7800) which plays an important role in bone metabolism. It has been shown to stimulate growth of cells in culture. Animal growth is also stimulated in pituitary deficient, normal and catabolic states. Kidney function is also improved. It can be produced using recombinant DNA technology, solid phase peptide synthesis, by isolating it from blood serum or from mammalian milk, e.g. bovine or human milk.

Immunoglobulins (IG) constitute a complex group of proteins, the elements of which are produced by B-lymphocytes; they make a significant contribution to the whey protein content—besides exerting an important immunological function. These proteins are present in the serum and physiological fluids of all mammals; some of them attach to surfaces, where they behave as receptors, whereas others function as antibodies, which are released in the blood, milk and lymph. IG are subject to postnatal transfer via colostrum—as the placenta does not permit passage of macromolecules. The structure and general function of IG is well described. In terms of quaternary structure, IG are either monomers or polymers of a four-chain molecule, consisting of two light polypeptide chains (with a molecular weight in Bovine Immunoglobulins of approximately 25,000 kDa) and two heavy chains (with molecular weight of 50,000-70,000 kDa). There are three major basic classes of IG: IGG, IGA and IGM, although IGG is often sub-divided into two subclasses—IGG1 and IGG2. Up to 80% (w/w) of all IG in milk or whey is accounted for by IGG but qualitatively, the family of IG found in bovine whey and colostrum include IGA and secretory IGA, IGG1, IGG2 and IGG fragments, IGM and IGE.

Osteopontin is an acidic, highly phosphorylated, sialic acid rich, calcium binding protein. Osteopontin contains approx. 28 moles of bound phosphate per mole osteopontin and binds approx. 50 moles of Ca per mole osteopontin. Osteopontin (OPN) is a multifunctional bioactive protein that is implicated in numerous biological processes, such as bone remodeling, inhibition of ectopic calcification, and cellular adhesion and migration, as well as several immune functions. Osteopontin has cytokine-like properties and is a key factor in the initiation of T helper 1 immune responses. Osteopontin is present in most tissues and body fluids, with the highest concentrations being found in milk. In the scientific literature osteopontin is typically purified from bone or milk and it is typically present in bovine milk in a concentration of 20 mg/L. In milk, osteopontin is a serum protein but may also to some extent associate with the casein micelles depending on the Ca2+ level. Acid whey is the preferred raw material for industrial production of osteopontin. When acid whey is formed osteopontin is thought to leave the casein micelles as Ca2+ leaks out into the serum phase. This aspect makes acid whey a straightforward source of osteopontin. For the same reason sweet whey has a slightly lower osteopontin content. Furthermore, sweet whey contains caseino macropeptide (CMP) from enzymatic cleavage of the kappa-casein. CMP has many biochemical resemblances with osteopontin—both are small, flexible, acidic, phosphorylated glycoproteins. For this reason CMP and osteopontin is believed to be quite similar in their binding to ion exchange resins, which will pose a problem in purifying osteopontin from a CMP-containing raw material. Another aspect is the likely degradation of osteopontin by proteolytic enzymes used for cheese making.

Separation of the individual whey protein factions have proven to be difficult due to the relatively similar physico-chemical properties of the different whey proteins. The skilled person knows that it is difficult to provide a good separation based on the molecular size of the whey proteins (as required when using membrane filtration) and the fractions provided in this way results in poor yields and/or poor purities because of the complexity of the whey material and the whey proteins to be isolated. However, separating whey proteins based on their isoelectric point (pI) gives two distinct groups: the major proteins, like alpha-lactalbumin; beta-lactoglobulin, immunoglobulin G and serum albumin, which are negatively charged at the pH of sweet whey (pH 6.2-6.4); and the minor whey proteins, like lactoferrin and lactoperoxidase, that hold a positive net charge at the pH of sweet whey. These distinct properties offer the possibility of selectively separating one group from another, using a chromatographic support. However, the use of adsorption chromatography for the industrial scale production of food and dietary proteins have proven difficult to establish commercially due to the high cost of chromatographic adsorbents, the low productivity associated with running adsorption columns and the high water and chemicals consumption associated with washing, eluting regenerating and cleaning chromatographic columns.

Milk and whey proteins occur naturally in mammalian milk including human milk and may be isolated and/or separated from these sources or any derivative hereof. However, certain proteins naturally present in milk, may also be present in other types of raw materials such as blood and plasma, mammalian tissue extracts and genetically modified plants, genetically modified algae and genetically modified microorganisms such as yeast and bacteria.

Accordingly, there is a need for methods for separating and/or isolating milk and whey proteins.

SUMMARY OF THE INVENTION

Thus, in a first aspect the present invention relates to a method for isolating one or more proteins naturally occurring in mammalian milk from an aqueous protein solution comprising said one or more proteins and impurities, the method comprising:

A. providing an aqueous solution containing the one or more proteins and the impurities B. adding a water-soluble silicate to the solution of step a) such that the total concentration of silicon in the form of free or complexed silicates in the solution is in the range of 1-750 mM, C. if necessary, adjusting the pH of the resulting solution to a pH in the range of pH 1 to pH 11, D. allowing the silicate to form an insoluble precipitate of a silicate-protein complex, E. separating the silicate-protein complex from the solution as a wet precipitate; such as a wet cake or an aqueous suspension of the precipitate, F. optionally washing the silicate-protein complex to further remove said impurities from the silicate-protein complex, G. optionally separating the one or more proteins from the silicate, thereby obtaining the isolated protein product.

Other aspects of the technology are evident from the appended claims and the following description.

LEGENDS TO THE FIGURES

FIGS. 1-12 show SDS-PAGE analyses of the various solutions of the respective examples

DETAILED DESCRIPTION OF THE INVENTION

Definitions

The term "Proteins naturally occurring in mammalian milk" means any protein or peptide that occurs in untreated milk from non-genetically modified mammals at a concentration of at least 1 microgram per litre.

The term "anionic compound" means a compound that comprise a negatively charged moiety at a pH in the range of pH 3 to pH 13.

The term "dry weight" means the weight or mass of a substance remaining after removal of water by heating to constant weight at 110 degrees Celcius. The dry weight per ml sample is thus the weight or mass of a substance remaining after removal of water by heating to constant weight at 110 degrees Celcius per ml sample applied to drying.

The term "isolating" or "separating" means any human intervention which change the relative amount of the compound compared to another selected constituent in a given matrix to a higher relative amount of the compound relative to the other constituent. In an embodiment, the compound may be isolated into a pure or substantially pure form. In this context, a substantially pure compound means that the compound preparation contains less than 10%, such as less than 8%, such as less than 6%, such as less than 5%, such as less than 4%, such as less than 3%, such as less than 2%, such as less than 1%, such as less than 0.5% by weight of other selected constituents. In an embodiment, an isolated compound is at least 50% pure, such as at least 60% pure, such as at least 80% pure, such as at least 90% pure, such as at least 91% pure, such as at least 92% pure, such as at least 93% pure, such as at least 94% pure, such as at least 95% pure, such as at least 96% pure, such as at least 97% pure, such as at least 98% pure, such as at least 99% pure, such as at least 99.5% pure, such as 100% pure by dry weight relative to other selected constituents.

The term "membrane separation process" refers to a process using a semi-permeable membrane, allowing only compounds having a size lower that a certain value to pass, to separate molecules of a higher size in a liquid or gas continuous phase composition from molecules of a lower size. In this context, liquid or gas continuous phase compositions are to be understood in the broadest sense, including both single phase compositions such as solutions or gases, and dual phase compositions such as slurries, suspensions or dispersions wherein a solid is distributed in a liquid or gas phase.

The term "retentate" means compounds which are not passing a selected membrane in a membrane separation process.

The term "permeate" or "filtrate" means compounds which pass a selected membrane in a membrane separation process.

The term "precipitation" refers to the phenomenon that a dissolved compound exceeding its solubility in the solvent undergoes a phase transition from a dissolved liquid state to a solid state. Precipitation is often caused by a chemical reaction and/or a change in the solution conditions. The solidified compound is referred to as the "precipitate".

The term "diafiltration" means a technique that uses ultrafiltration membranes to completely remove, replace, or lower the concentration of salts or solvents from solutions containing proteins, peptides, nucleic acids, and other biomolecules. The process selectively utilizes permeable (porous) membrane filters to separate the components of solutions and suspensions based on their molecular size. An ultrafiltration membrane retains molecules that are larger than the pores of the membrane while smaller molecules such as salts, solvents and water, which are 100% permeable, freely pass through the membrane. In a diafiltration process the retentate is added water or a buffer composition while the membrane filtration process continuously removes water, salts and low molecular weight compounds to the permeate side of the membrane.

The term "adsorption" means a process in which molecules from a gas, liquid or dissolved solid adhere to a surface of a solid phase adsorbent. Likewise, and adsorbent (also named a solid phase adsorbent) is an insoluble material on which adsorption can occur.

The term "protein" means macromolecules consisting of one or more long chains of amino acid residues. In the context of this invention the term "protein" covers any chain length and thus includes small peptides and polypeptides.

The term "protein concentration" means the amount of protein per litre of a sample calculated as the total weight or mass of amino acids per liter as determined according to EUROPEAN PHARMACOPOEIA 5.0 section 2.2.56. AMINO ACID ANALYSIS or by determination of total nitrogen in a sample by the method of Kjeldahl using the conversion factor N×6.25. All samples are dialyzed against demineralized water in dialysis tubing cellulose membrane (Sigma-Aldrich, USA, cat. No.: D9652) to remove any free amino acids and low molecular weight peptides prior to the amino acid determination.

The term "soluble" means solubility in water at a concentration of at least 1 g/L at 25 degrees Celsius.

The term "comprise" and "include" as used throughout the specification and the accompanying items/claims as well as variations such as "comprises", "comprising", "includes" and "including" are to be interpreted inclusively. These words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The key findings of the present invention are that adjustment of the pH of a solution comprising one or more proteins naturally occurring in mammalian milk, silicate and impurities allows for a selective and reversible precipitation and separation of a silicate-protein complex. The protein can therefore be separated from the impurities using selective silicate complex formation and the reversible nature of the precipitation enables the subsequent separation of the protein from the silicate.

The protein isolated according to the invention has high purity and high functionality due to the gentle nature of the methodology.

A first method for isolating one or more proteins naturally occurring in mammalian milk from an aqueous protein solution comprising said one or more proteins and impurities is thus provided, the method comprising;

A. providing an aqueous solution containing the one or more proteins and the impurities B. adding a water-soluble silicate to the solution of step A) such that the total concentration of silicon in the form of free or complexed silicates in the solution is in the range of 1-750 mM, C. if necessary, adjusting the pH of the resulting solution to a pH in the range of pH 1 to pH 11, D. allowing the silicate to form an insoluble precipitate of a silicate-protein complex, E. separating the silicate-protein complex from the solution as a wet precipitate; such as a wet cake or an aqueous suspension of the precipitate, F. optionally washing the silicate-protein complex to further remove said impurities from the silicate-protein complex, G. optionally separating the one or more proteins from the silicate, thereby obtaining the isolated protein product.

In one aspect, said washing step F) is mandatory. In another aspect, said separating step G) is mandatory. Said first method may further comprising a step of clarification to remove insoluble and/or colloid particles prior to step B).

The separation of the silicate-protein complex from the solution in step E above may be performed by physical methods like filtration or sedimentation methods. In a preferred embodiment the solution and the silicate-protein complex is separated by way of centrifugation in a decanter. In a preferred embodiment the separation is performed in a hydrocyclone. In a preferred embodiment the solution and the protein-silicate complex is separated by way of filtration in a tangential flow membrane system such as a hollow fiber, tubular membrane, flat sheet or spiral wound membrane system employing ceramic or organic polymer membranes. In a preferred embodiment the membrane employed has a pore size in the range of 5-2000 nm, such as 10-1500 nm, such as 10-100 nm, such as 20-1200 nm, such as 50-1000 nm, such as 100-500 nm.

In said method, separation of the one or more proteins from the silicate may be done by adjusting the pH of the wet precipitate to a pH in the range of pH 6 to pH 13, such as a pH in the range of pH 6.5-pH 12, such as a pH in the range of pH 7-pH 11, such as a pH in the range of pH 7.5-pH 11, such as a pH in the range of pH 8-pH 11, such as a pH in the range of pH 8 to pH 9, such as a pH in the range of pH 8.5 to pH 11, such as a pH in the range of pH 8.5 to pH 9.9, such that the one or more proteins are released into solution from the precipitate while at least 50% of, such as at least 60%, such as at least 70%, such as at least 80% such as at least 85% such as at least 90%, such as at least 95% of the silicate in the protein-silicate complex remains in the form of an insoluble precipitate.

In said method the separation of the one or more proteins from the silicate may further be done by adjusting pH to below pH 5.0 such as a pH in the range of 0.1 to 4.9, such a pH in the range of pH 0.5 to pH 4.0, such as a pH in the range of 0.9 to pH 4.2, such as a pH in the range of 1.5 to pH 3.8, such as a pH in the range of pH 1.9 to pH 3.2, such as a pH in the range of 2.2 to pH 3.0 such that the one or more proteins are released into solution from the precipitate while at least 50% of, such as at least 60%, such as at least 70%, such as at least 80% such as at least 85% such as at least 90%, such as at least 95% of the silicate in the protein-silicate complex remains in the form of an insoluble precipitate.

The further separation of the one or more proteins thus released into solution while the silicate remains fully or partly insoluble may be performed by physical methods like filtration or sedimentation methods. In a preferred embodiment the solution and the insoluble silicate is separated by way of centrifugation in a decanter. In a preferred embodiment the solution and the insoluble silicate is separated by way of filtration in a tangential flow membrane system such as a hollow fiber, tubular membrane, flat sheet or spiral wound membrane systems including ceramic or organic polymer membranes. In a preferred embodiment the membrane employed has a pore size in the range of 5-2000 nm, such as 10-1500 nm, such as 10-100 nm, such as 20-1200 nm, such as 50-1000 nm, such as 100-500 nm.

In said method the separation of the one or more proteins from the silicate may further be done by first adjusting the pH of the wet precipitate to a pH in the range of pH 9 to pH 13, such as pH 9.5 to pH 12.5, such as pH 9.5 to pH 12.0, such as pH 9.5 to pH 11.5 such as pH 10.0 to pH 11.9 to solubilize the silicate-protein complex followed by allowing the silicate to be separated from the protein by a method selected from the group consisting of membrane filtration such as ultrafiltration using a membrane allowing the selective passage of silicate ions, selective silicate precipitation with metal-ions, selective precipitation of the protein with organic solvents, polymers or lyotropic salts, and adsorption chromatography such as ion exchange.

In a preferred embodiment the separation and washing steps E, F and G are all performed by way of tangential flow membrane filtration, preferably employing a hollow fibre, tubular membrane, flat sheet or spiral wound membrane system including ceramic or organic polymer membranes. In a preferred embodiment the membranes employed have a pore size in the range of 5-2000 nm, such as 10-1500 nm, such as 10-100 nm, such as 20-1200 nm, such as 50-1000 nm, such as 100-500 nm.

In a preferred embodiment the method is carried out as a continuous process, including inline addition of silicates, inline pH adjustment, and inline washing steps as necessary and relevant for the specific embodiment.

In a preferred embodiment the pH of the solution in step C is adjusted to a pH in the range 2-11, such as e.g. 4-9, such as e.g. 4.5-8, such as e.g. 5-6.

In a preferred embodiment the one or more proteins are selected from the group of alpha-lactalbumin, beta-lactoglobulin, lactoferrin, lactoperoxidase.

In a preferred embodiment the one or more proteins are selected from the group of osteopontin, angiogenin, immunoglobulin G, immunoglobulin A, plasminogen, whey acidic protein (WAP), alkaline phosphatase, acid phosphatase, xanthin oxidoreductase, catalase, albumin.

In a preferred embodiment the one or more proteins are selected from the group of caseins and casein peptides such as casein glycomacropeptide.

In a preferred embodiment the one or more proteins are selected from the group of growth factors such as the insulin-like IGF-I, IGF-II, epidermal growth factor EGF, transforming growth factors TGF-β1 and TGF-β2, the basic fibroblast growth factor bFGF and the platelet-derived growth factor PDGF.

In a preferred embodiment the aqueous solution containing the one or more proteins and the impurities is selected from the group of milk and whey and concentrates and derivatives hereof.

In a preferred embodiment the aqueous solution containing the one or more proteins and the impurities is selected from the group of sweet whey, acid whey, native whey from microfiltration of milk, salty whey from brined cheeses, and concentrates and other derivatives hereof.

In a preferred embodiment the aqueous solution containing the one or more proteins and the impurities is selected from the group of extracts of genetically modified plants including algae, extracts and culture supernatants from genetically modified microorganisms including genetically modified yeasts and bacteria and derivatives hereof.

In a preferred embodiment said one or more proteins are one or more first proteins, and said impurities comprise one or more second proteins, such that the method provides the separated one or more first proteins and said one or more second proteins in two different fractions.

In a preferred embodiment said one or more first proteins comprise betalactoglobuline and said one or more second proteins comprise alpha-lactalbumin, such that the method provides beta-lactoglobulin and alpha-lactalbumin in two different fractions. In a preferred embodiment the alpha-lactalbumin fraction contains less than 50%, such as less than 40%, such as less than 30%, such as less than 20%, such as less than 10%, such as less than 5% beta-lactoglobulin relative to alpha-lactalbumin on a dry matter basis. In a preferred embodiment the beta-lactoglobulin fraction contains less than 10%, such as less than 5%, such as less than 2%, such as less than 1% alpha-lactalbumin relative to beta-lactoglobulin on a dry matter basis.

Silicate-Protein Complexes and their Use

Further, the silicate-protein complexes created during the separation process according to the invention may themselves constitute novel products with valuable properties and it is therefore, in some preferred embodiments, an option to omit the separation of the silicate from the protein.

Thus, the present invention further provides a silicate-protein complex comprising silicate complexed together with one or more proteins naturally occurring in mammalian milk.

Such a product can be obtained by the method above, wherein step G is omitted.

In a broader perspective the invention further provides a novel type of silicate-protein complex product produced by a method wherein, I. an aqueous solution containing one or more proteins, and optionally impurities, is added a water-soluble silicate such that the total concentration of silicon in the form of free or complexed silicates in the solution is in the range of 1-750 mM, II. if necessary, adjusting the pH of the resulting solution to a pH in the range of pH 1 to pH 11, III. allowing the silicate to form an insoluble precipitate of a silicate-protein complex, IV. separating the silicate-protein complex from the solution as a wet precipitate; such as a wet cake or an aqueous suspension of the precipitate, V. optionally washing the silicate-protein complex to further remove said impurities from the silicate-protein complex, VI. optionally drying the silicate-protein complex thereby obtaining the isolated silicate-protein complex product.

In a preferred embodiment the silicate-protein complex has a molar silicon to protein nitrogen ratio (Si:N) in the range of 20:1 to 1:3; such as 15:1 to 1:2; such as 10:1 to 1:2; such as 5:1 to 1:2; such as 4:1 to 1:2; such as 3:1 to 1:2; such as 2:1 to 1:2; such as 2:1 to 1,5; such as 2:1 to 1:1.

All details above of the method, which relate to the nature of the proteins are also relevant for the silicate-protein complex.

For instance, the one or more proteins in the protein-silicate complex may be selected from lactalbumin, beta-lactoglobulin, lactoferrin, lactoperoxidase.

In a preferred embodiment the one or more proteins are selected from the group of osteopontin, angiogenin, immunoglobulin G, immunoglobulin A, plasminogen, whey acidic protein (WAP), alkaline phosphatase, acid phosphatase, xanthin oxidoreductase, catalase, albumin.

In a preferred embodiment the one or more proteins are selected from the group of caseins and casein peptides such as casein glycomacropeptide.

In a preferred embodiment the one or more proteins are selected from the group of growth factors such as the insulin-like IGF-I, IGF-II, epidermal growth factor EGF, transforming growth factors TGF-β1 and TGF-β2, the basic fibroblast growth factor bFGF and the platelet-derived growth factor PDGF.

Similarly, all details of the silicates set out below are relevant for the silicate-protein complex of the invention.

In one aspect the silicate-protein complex may be used as a feed ingredient, a food ingredient, or in the food or feed industry.

In one aspect the silicate-protein complex may be used as an additive as an anti-caking agent in the drying process for other proteins such as milk and whey protein concentrates and plant proteins such as soy, pea and potato proteins.

In one aspect the silicate-protein complex may be used as a controlled release reagent.

Thus, in one aspect the silicate-protein complex may be used as a controlled release reagent in chewing gums comprising bioactive components. In one aspect the bioactive components comprise non-protein bioactive components.

In a further aspect the silicate-protein complex comprises one or more growth factors such as the insulin-like IGF-I, IGF-II, epidermal growth factor EGF, transforming growth factors TGF-β1 and TGF-β2, the basic fibroblast growth factor bFGF and the platelet-derived growth factor PDGF. In an embodiment such silicate-protein complex comprising growth factors is used for treatment of inflammatory gastrointestinal disorders, wound healing, bone tissue regeneration or skin diseases.

In a further aspect the silicate-protein complex comprises one or more antimicrobial proteins such as lactoferrin, lactoperoxidase, immunoglobulins, transferrin and lysozyme. In an embodiment the antimicrobial protein is selected from the group of avidin, ovotransferrin, interferons, defensins, cathelicidins, protegrins, bactericidal/permeability-increasing protein (BPI), S100 proteins (e.g., calprotectin) and RNAses. In an embodiment such silicate-protein complex is used as a healthcare product, a cosmetic product, a dietary supplement or a pharmaceutical product. In an embodiment such silicate-protein complex is used as an ingredient in chewing gum, tooth paste, ointments for skin care, shampoos.

In an embodiment such silicate-protein complex comprising antimicrobial proteins is used for treatment or prevention of inflammatory gastrointestinal disorders, wound healing or skin diseases. In a further embodiment such silicate-protein complex comprising antimicrobial proteins is used for the treatment or prevention of gastrointestinal disorders of weaning farm animals such as piglets and calves.

In an embodiment the silicate-protein complex comprise immunoglobulins directed towards specific disease agents. In an embodiment the immunoglobulins are produced by vaccination of a mammal. In an embodiment the immunoglobulins are isolated from human or animal blood plasma. In an embodiment the immunoglobulins are isolated from cell cultures such as mammalian cell cultures producing monoclonal antibodies. In an embodiment the immunoglobulins are isolated from egg yolk.

Periodontal disease is a chronic inflammatory process that leads to the destruction of gingival connective tissue and alveolar bone and eventually causes loss of teeth. Recent evidence suggests that periodontal disease is a potential risk factor for several systemic diseases including cardiovascular disease, diabetes, stroke and preterm low birthweight. Gingivitis is one of the commonest forms of periodontal disease and one of the most widespread human infectious diseases. Although several factors are associated with gingivitis, bacterial infection is considered to be the leading cause. Gingivitis is characterized by dental plaque, which mainly composed of gram-negative strict anaerobes such as *Prevotella intermedia, Porphyromonas gingivalis* and *Fusobacterium nucleatum. P. intermedia* is one of these potential periodonto pathogenic bacterial species and *P. intermedia* cells are frequently recovered from subgingival flora in patients with acute necrotizing ulcerative gingivitis and pregnancy gingivitis. It is generally accepted that lowering the oral bacterial biomass is an effective method for curing and preventing gingivitis. Antimicrobials, along with mechanical therapy (such as scaling and root planing), are commonly used in the treatment of periodontal disease, but synthetic antimicrobials (antibiotics) are not available for some sufferers of gingivitis, such as pregnant women, the high-risk groups of gingivitis, because of the potential side effects. And the increasing prevalence of antibiotic-resistant bacteria has greatly reduced the applicability of antibacterial therapy. Therefore, alternative therapies for gingivitis are urgently needed.

Thus, in a preferred embodiment the silicate-protein complex comprise immunoglobulins directed towards microorganisms causing gingivitis and other periodontal diseases such as *Streptococcus mutans, Solobacterium moorei, Porphyromonas gingivalis, Fusobacterium Nucleatum* and *Prevotella intermedia.*

For most of the mentioned uses of a silicate-protein complex it is a requirement that the product is non-toxic, edible and preferably based on raw materials of GRAS status (generally accepted as safe for human consumption). Thus, in a preferred embodiment the silicate:protein complex is prepared by the use of water soluble inorganic silicates approved as food additives, such as sodium silicates in either solid or liquid form (water glass).

Silicates

A silicate in the context of the present invention is an anionic compound containing covalently linked silicon and oxygen. Any water-soluble silicate may be employed according to the invention. Particularly preferred are the alkali metal silicates including sodium silicate which is the common name for compounds with the formula $Na_2(SiO_2)_nO$. A well-known member of this series is sodium metasilicate, $Na_2SiO_3$. Also, known as water glass or liquid glass, these materials are available in aqueous solution and in solid form.

The silicate concentration is in the range of 0.5-50 g/L. In the present context it may preferably be in the range of 0.5-25 g/L, 0.5-17 g/L, 1-15 g/L, 1-12 g/L, 1-10 g/L, 1-8 g/L, 1.5-20 g/L, 1.5-15 g/L, 1.5-12 g/L, 2-20 g/L, 2-15 g/L, 2-12 g/L, 2.5-20 g/L, 2.5-15 g/L, or 2.5-12 g/L. The silicate concentration may be in the range of 3-15 g/L, preferably in the range of 3-12 g/L.

In one embodiment of the invention the silicate may be an organosilicate (organosilanol) comprising a silicon covalently coupled to an organic molecule through a carbon-silicon bond wherein the organic molecule is capable of binding proteins in a reversible and selective manner.

In one embodiment the organosilicate is prepared by reaction of an organic molecule with a functional silane compound followed by hydrolysis to create the organosilicate.

In one embodiment the functional silane is chosen from the group of: glycidoxypropyltrimethoxysilane, glycidoxypropyltriethoxysilane, 3-glycidoxypropylmethyldiethoxysilane aminopropyltrimethoxysilane, aminopropyltriethoxysilane, N-(2-aminoethyl)-3-aminopropyl-trimethoxysilane, 3-methacryloxypropyltrimethoxysilane, 3-mercaptopropyltrimethoxysilane, 6 vinyltrimethoxysilane In preferred embodiments the organic molecule is a positively or negatively charged molecule.

In a preferred embodiment the organic molecule is a hydrophobic molecule comprising one or more aromatic rings.

In a preferred embodiment the organic molecule comprises one or more aromatic rings and one or more acidic groups.

In a preferred embodiment the organic molecule comprises a benzoic acid derivative such as 4-aminobenzoic acid, mercaptobenzoic acid and hydroxybenzoic acid.

In a preferred embodiment the ligand comprises an aromatic amine such as benzylamine.

In a preferred embodiment the organic molecule comprises an alkyl-amine such as butylamine hexylamine and octylamine.

In a preferred embodiment the organic molecule is covalently coupled to an activated silane compound, such as glycidoxypropyltrimethoxysilane In a preferred embodiment the organo-silicate is mixed with an inorganic silicate in order to selectively precipitate one or more protein from a solution according to the invention.

EXAMPLES

Abbreviations

Alpha-la=alpha-lactalbumin
Beta-lg=beta-lactoglobulin
GMP=glycomacropeptide

IgG=Immunoglobulin G
BSA=bovine serum albumin
LF=lactoferrin

Materials and Methods

Chemicals used in the examples herein e.g. for preparing buffers and solutions are commercial products of at least reagent grade.

Waterglass, sodium metasilicate used for precipitation of proteins was from Borup Kemi, Denmark, with the following specifications: 36° BE, Silicate concentration as $SiO_2$=25-26% and $Na_2O$=7.5-8.5° h.

Water used for conducting the experiments is de-ionized water

Acidic Whey:

Acidic whey obtained from a local dairy, as a by-product from yoghurt production (test solution 1) with a pH of 4.6 and a conductivity of 7.5 mS/cm, measured with a Seven2Go S3 conductivity meter from Mettler Toledo, Switzerland.

Casein Whey:

Skim milk obtained from local supermarket was heated to 35° C. and pH adjusted to pH 4.5-4.6 with 1 M hydrogen chloric acid to precipitate the caseins. After pH adjustment, the milk was centrifuged for 10 min at 1430 G and the supernatant was collected=casein whey (test solution 2). pH in the casein whey is 4.65 and the conductivity is 9.5 mS/cm, measured with a Seven2Go S3 conductivity meter from Mettler Toledo, Switzerland.

Microfiltrated Whey (Native Whey from Microfiltrated Milk):

Skim milk from a local supermarket was micro filtered on a 0.2 μm hollow fiber membrane. The caseins and a fraction of the whey proteins are recovered in the retentate. A fraction of the whey proteins mainly beta-lactoglobulin (beta-lg) and alpha-lactalbumin (alpha-la) are recovered in the permeate=microfiltrated whey (test solution 3)

Sweet Whey:

Sweet whey obtained from a local dairy, as a by-product from cheese production (test solution 4) with a pH of 6.3 and a conductivity of 5 mS/cm, measured with a Seven2Go S3 conductivity meter from Mettler Toledo, Switzerland.

Concentrated Casein Whey:

Casein whey was concentrated on a 10 kD hollow fiber membrane 2.5 times (see description of ultrafiltration below): 10 L test solution 2 was applied to the filter. When 6 L of permeate was collected the concentration was stopped and the retentate was collected for experiments (test solution 5).

Demineralised Concentrated Casein Whey:

Concentrated casein whey was dialysed against water to removed ions such as calcium and magnesium ions. 150 ml test solution 5 was dialysed using dialysis tubing cellulose membrane (Sigma-Aldrich, USA, cat. No.: D9652) against 10 L of demineralized water for 18 hours. Volume after dialysis=156 ml. (test solution 6)

The resulting pH was 5.0 and the conductivity was 83 μS/cm, measured with a Seven2Go S3 conductivity meter from Mettler Toledo, Switzerland.

Demineralised Casein Whey:

Casein whey was dialysed against 50 mM NaCl solution to mainly remove calcium and magnesium ions. 33 ml of test solution 2 was dialysed against 5 L of 50 mM NaCl for 18 hours.

Volume after dialysis=42 ml (test solution 7).

Buffer Solutions 50 mM NaCl 2.92 g NaCl

Up to 1 L with water 0.1 M NaCl 5.84 g NaCl up to 1 L with water 0.25 M NaCl 14.61 g NaCl Up to 1 L with water 0.5 M NaCl 29.44 g NaCl Up to 1 L with water 1 M NaOH 40 g NaOH Up to 1 L with water 5 M NaOH 200 g NaOH Up to 1 L with water SDS-PAGE Electrophoresis Reagents a) LDS sample buffer, 4× is obtained from Expedeon, USA (Cat. no.: NXB31010)

b) SDS Run buffer, 20× is obtained from Expedeon, USA (Cat. no.: NXB50500)

c) Precast 4-20% gradient gels are obtained from Expedeon, USA (Cat. no.: NXG42012K)

d) Instant Blue Coomassie staining solution is obtained from Expedeon, USA (Cat. no. ISB1L).

Assays a) SDS-PAGE Electrophoresis

The samples produced in each example are analyzed using SDS-PAGE gel electrophoresis showing the protein composition in each sample. The SDS-PAGE gel electrophoresis is performed using an electrophoresis apparatus and precast 4-20% gradient gels from Expedeon USA (Cat. no.: NXG42012K). The protein samples are mixed with LDS sample buffer and incubated for 10 minutes at 70° C. The samples are applied to a precast gel and proteins are allowed to run for one hour at 200 V 90 mA in the SDS Run buffer at non-reduced running conditions. The gel is developed in the staining solution for three hours and the protein bands are evaluated by visually inspection or analyzed by scanning densitometry to quantify the amount of specific proteins in the test solutions.

b) Dry Matter Determination

A Sartorius moisture analyzer (MA37, Sartorius) is used to determine dry matter in a sample by applying 5-10 mL of a sample to the instrument. The sample is then dried at 110° C. until constant weight and the remaining dry matter is determined and calculated by the instrument.

c) Moisture Determination

The moisture of a freeze dried sample was determined with the following method: 0.5 g of freeze dried sample was applied to the Sartorius moisture analyzer instrument. The sample is then dried at 110° C. until constant weight and the remaining dry matter is determined and calculated by the instrument. The moisture is calculated as: 100%–the dry matter percentage.

d) Silicate Content

To determine silicate content an assay from Merck Millipore, USA was used (cat. No.: 1.00857.0001).

In sulfuric acid solution silicate ions react with molybdate ions to form a yellow solution that is determined photometrically at 410 nm.

2 ml sample,

100 µl Si1-solution and 1 ml Sit-solution

The solution is mixed well and incubated for 2 min.

100 µl Si3-solution is added and mixed well and incubated for 2 min

The solution is measure with a spectrophotometer (Biobase BK-UV1800, China) at 410 nm.

e) Protein Determination.

The content of nitrogen in selected samples was determined with elementary analysis. The protein content was calculated by multiplying the percentage of nitrogen with a factor of 6.25. All samples are initially dialyzed against demineralised water in dialysis tubing cellulose membrane (Sigma-Aldrich, USA, cat. No.: D9652) to remove any free amino acids and low molecular weight peptides.

Ultrafiltration

Samples are ultrafiltrated using a system from Spectrum Labs, USA, fitted with KrosFlo TFF system KMOi using hollow fiber ultrafiltration membranes. A membrane cut-off value of 10 kDa and membrane area of 1.25 m2 is employed (Spectrum Labs, USA cat. no.: K02-E010-05-N).

Figure 1B:
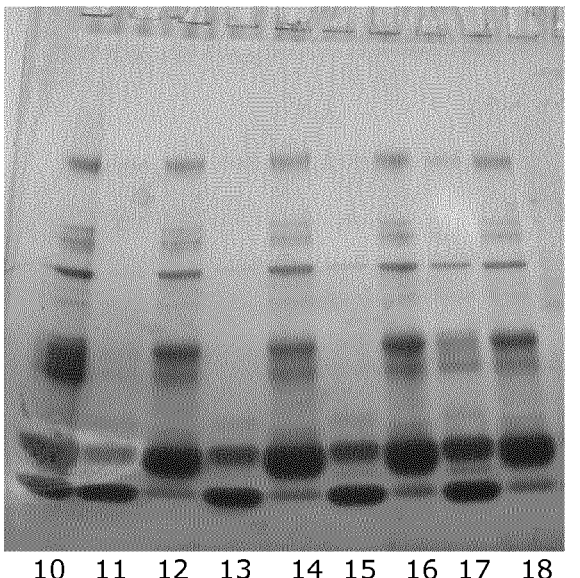

Example 1. Isolating Whey Proteins from Sweet Whey Using Silicate at Different pH-Values 80 ml of sweet whey (test solution 4) is divided into 8 samples (A through H respectively) of 10 ml whey, 0.2 ml of waterglass is added to each sample. pH is adjusted with 1 M HCl to A: pH 3.0, B: pH 3.5, C: pH 4.0, D: pH 4.5, E: pH 5.0, F: pH 5.5, G: pH 6.0, H: pH 6.5. Following incubation for 30 minutes with stirring at ambient temperature the samples are centrifuged for 10 min at 1430 G and the supernatants (test solutions 5-12) separated from the precipitates. The precipitate remaining in the centrifuge tube is washed by re-suspending in 10 ml water and then centrifuged again. The proteins are released from the precipitate by adding 9.5 ml of water, while mixing the pH is raised to 12.5 by adding 1 M NaOH (test solutions 13-20) SDS-PAGE is performed on test solution 4-20 as illustrated in FIGS. 1A and 1B.

FIG. 1A:

Lane 1: Test solution 4, Sweet whey

Lane 2: Test solution 5, supernatant pH 3.0

Lane 3: Test solution 13, dissolved precipitate from pH 3

Lane 4: Test solution 6, supernatant pH 3.5

Lane 5: Test solution 14, dissolved precipitate from pH 3.5

Lane 6: Test solution 7, supernatant pH 4.0

Lane 7: Test solution 15, dissolved precipitate from pH 4.0

Lane 8: Test solution 8, supernatant pH 4.5

Lane 9: Test solution 16, dissolved precipitate from pH 4.5

FIG. 1B:

Lane 10: Test solution 4, Sweet whey

Lane 11: Test solution 9, supernatant pH 5.0

Lane 12: Test solution 17, dissolved precipitate from pH 5.0

Lane 13: Test solution 10, supernatant pH 5.5

Lane 14: Test solution 18, dissolved precipitate from pH 5.5

Lane 15: Test solution 11, supernatant pH 6.0

Lane 16: Test solution 19, dissolved precipitate from pH
6.0

Lane 17: Test solution 12, supernatant pH 6.5

Lane 18: Test solution 20, dissolved precipitate from pH
6.5

The SDS PAGE analysis of FIGS. 1A and 1B, illustrates
that in the pH-range of 5.0 to 6.0 the sodium metasilicate
solution is capable of precipitating the major part of the
proteins present in the sweet whey except the alpha-la—see
lane 11, 13 and 15 resulting in a highly enriched alpha-la
product, there is no IgG, LF, BSA present in the product. The
alpha-la product contains the GMP and a very small amount
of beta-lg.

At pH 3.0 and 3.5 hardly any protein precipitates with the
sodium metasilicate, see lane 3 and 5.

At pH 4 and 4.5 the sodium metasilicate starts to precipi-
tate a minor fraction of the beta-lg, BSA and LF, see lane 7
and 9. More protein is precipitated at pH 4.5 than at 4.0.

At pH 6.5 more beta-lg, BSA and IgG appear in the
alpha-la enriched product, see lane 17.

Example 2. Isolation of LF from Acid Whey Using Silicate 960 ml acidic whey (test solution 1) is mixed 4.8 ml
waterglass. The solution is incubated for 1 hr at room
temperature. Following incubation, the sample is centri-
fuged for 10 min at 1430 G and the supernatant (test solution
2) is separated from the precipitate. The precipitate remain-
ing in the centrifuge tube is re-suspended in 100 ml water
and then centrifuged again. 50 ml of water is added to the
precipitate and the precipitate is dissolved by increasing pH
to 10 with 1 M NaOH (test solution 3)

Figure 2:
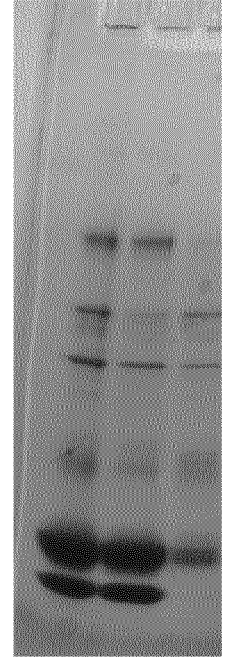

SDS-PAGE is performed on test solutions 1, 2 and 3 as
illustrated in FIG. 2.

FIG. 2:

Lane 1: Acidic whey, test solution 1

Lane 2: Supernatant, test solution 2

Lane 3: dissolved precipitate pH 10, test solution 3

The SDS PAGE analysis of FIG. 2, illustrates that the
sodium metasilicate solution does not precipitate significant
amounts of protein present in the acidic whey—see lane 2
which shows that most of the bands representing the differ-
ent proteins have the same intensity for the supernatant as
for the acidic whey (see lane 1). The silicate precipitates the
LF (lactoferrin) resulting in a highly LF enriched product,
containing only a small fraction of the BSA (serum albumin)
and beta-lg (see lane 3). The silicate does not precipitate the
alpha-la at all (see lane 3).

Figure 3:
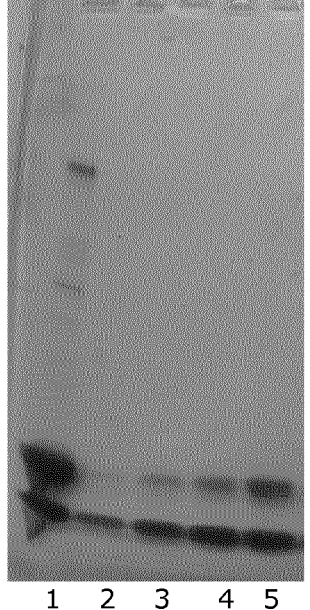

Example 3. Isolating Whey Proteins from Acidic Whey from Yoghurt Production Using Different Concentrations of Silicate 40 ml of LF depleted acidic whey (produced according to
example 2, test solution 2) is divided into 4 samples (A
through D respectively) of 10 ml whey, different amounts of
waterglass are added. A: 666 µl, B: 333 µl, C: 111 µl, D: 83
µl. pH was adjusted in all solutions to 6.0 with 1 M HCl.
Following incubation for 60 minutes with stirring at ambient
temperature the samples are centrifuged for 10 min at 1430
G and the supernatants (test solutions 3-6) separated from
the precipitates. SDS-PAGE is performed on test solution
2-6 as illustrated in FIG. 3.

FIG. 3:

Lane 1: Test solution 2, LF depleted acidic whey from
yoghurt production

Lane 2: Test solution 3, supernatant from 666 µl water-
glass per 10 ml acidic whey Lane 3: Test solution 4, supernatant from 333 µl water-
glass per 10 ml acidic whey Lane 4: Test solution 5, supernatant from 111 µl water-
glass per 10 ml acidic whey Lane 5: Test solution 6, supernatant from 83 µl waterglass
per 10 ml acidic whey The SDS PAGE analysis of FIG. 3, illustrates that all the
tested concentrations of sodium metasilicate results in a
highly enriched alpha-la fraction where only beta-lg is
present in different supernatants. A high concentration of
sodium metasilicate (666 µl per 10 ml acidic whey) is
capable of precipitating the major part of the proteins
present in the LF depleted acidic whey—see lane 2, though
there is still a small fraction of the alpha-la left in the
supernatant. When the concentration of silicate is decreased
especially the alpha-la starts to appear in the supernatant, for
111 and 83 µm water glass per 10 ml whey no alpha-la
precipitates, the intensity of the alpha-la band is the same as
for the LF depleted acidic whey (see lane 4 and 5 compared
with lane 1). With a decrease of silicate concentration also
more beta-lg appear in the supernatant (see lane 5 compared
to lane 3 and 4). Test solution 5 (see lane 4) contains alpha-la
and a minor fraction of beta-lg, there is no BSA, LF or
immunoglobulin present, resulting in a highly enriched
alpha-la product.

Example 4. Isolating Whey Proteins from Acidic Whey from Yoghurt Production Using Silicate 350 ml of LF depleted acidic whey (produced according
to example 2, test solution 2) is mixed with 3.9 ml of silicate
at 25° C. pH is adjusted to a final pH value of 6.0 with 1 M
HCl solution. Following incubation for 60 minutes with
stirring at ambient temperature the sample is centrifuged for
10 min at 1430 G and the supernatant (test solution 3) is
separated from the precipitate.

The precipitate remaining in the centrifuge tube is washed
by re-suspending in 45 ml water and then centrifuged again.
This procedure is repeated twice. Following the last cen-
trifugation, the water wash supernatants are mixed with test
solution 3.

The proteins are released from the precipitate by adding
175 ml 0.1 M NaCl, while mixing the pH is raised to 10.0.
The sample is centrifuged for 10 min at 1430 G and the
supernatant (test solution 4) is separated from the precipi-
tate. Another 56 ml of 0.1 M NaCl is added and pH is
adjusted to 10.0 while mixing. The sample is centrifuged for
10 min at 1430 G and the supernatant is pooled with test
solution 4, pH in test solution 4 is adjusted to 7.0 with 1 M
HCl. Test solution 4 was dialysed against 50 mM NaCl to
remove silicate using a dialysis tube (Cellulose membrane
14 kD cut off, Sigma-Aldrich, USA cat. no.: D9652). The
precipitate remaining in the test tube is dissolved by adding
56 ml water and during mixing the pH is adjusted to 12 with
1 M NaOH, test solution 5.

Figure 4:
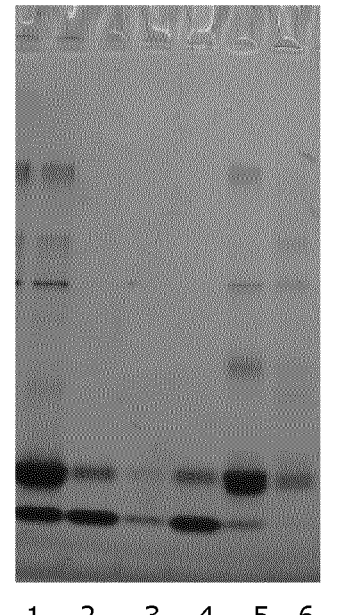

SDS-PAGE is performed on test solutions 2 to 5 as
illustrated in FIG. 4.

Dry matter is determined in test solution 4 after dialysis.

Silicate test was performed on test solution 3, 4 (before
and after dialysis) and 5

FIG. 4:

Lane 1: LF depleted acidic whey from yoghurt produc-
tion, test solution 2

Lane 2: Supernatant after precipitation with silicate, test
solution 3

Lane 3: Wash fraction

Lane 4: Pool of test solution 3 and wash fraction

Lane 5: Released proteins from silicate precipitate at pH 10.0, test solution 4

Lane 6: Dissolved silicate precipitate, test solution 5

The SDS PAGE analysis of FIG. 4, illustrates that the sodium metasilicate solution is capable of precipitating all the protein present in the acidic whey except alpha-la—see lane 2 which shows that only a very small fraction of the beta-lg and most of the alpha-la is in test solution 3, resulting in a highly enriched alpha-la product. Further, it is seen that after washing of the precipitate with water practically all the precipitated proteins are released in one pool at pH 10 (see lane 5) while it is important to note that also at this pH the silicate is still precipitated. There is practically no protein left in the precipitate when dissolved at pH 12 (see lane 6) since very weak bands are showing.

Dry matter result on dialysed test solution 4 shows that 3.4 mg dry matter is removed per ml acidic whey.

Silicate test shows that the concentration of silicate in test solution 3 (alpha-la enriched product) is 12.7 times lower than in test solution 5 (dissolved silicate precipitate) meaning that more than 90% of the applied silicate precipitates together with the major part of the proteins. This small amount of silicate can be removed when the alpha-la enriched product is further processed with ultrafiltration and diafiltration.

The concentration of silicate in the released protein product at pH 10, test solution 4 is about 11 times lower than in test solution 5 (dissolved silicate precipitate). The dialysed test solution 4 does not contain silicate, no yellow color appears when mixing the sample with the different test chemicals.

The dissolved silicate precipitate, test solution 5, can be used in another cycle to precipitate whey proteins in acidic whey.

Example 5. Isolating Whey Proteins from Casein Whey Using Silicate

A two-step procedure was performed where in step 1: LF is isolated. In step 2: An alpha-la enriched fraction is produced together with an enriched beta-lg fraction.

Step 1: LF is isolated with silicate: 500 ml casein whey (test solution 2) is mixed 2.5 ml water glass. The solution is incubated for 1 hr at room temperature. Following incubation, the sample is centrifuged for 10 min at 1430 G and the supernatant (test solution 3) is separated from the precipitate. The precipitate is washed with water. 50 ml of water is added to the washed precipitate and pH is adjusted to 12 to dissolve the precipitate (test solution 4).

Step 2: 50 ml of LF depleted casein whey (test solution 3) is mixed with 0.55 ml of water glass at 25° C. pH is adjusted to a final pH value of 6.0 with 1 M HCl solution. Following incubation for 60 minutes with stirring at ambient temperature the sample is centrifuged for 10 min at 1430 G and the supernatant (test solution 5) is separated from the precipitate.

The precipitate remaining in the centrifuge tube is washed by re-suspending in 45 ml water (total volume of 50 ml) and then centrifuged again, the supernatant is removed (test solution 6).

The proteins are released from the precipitate by adding 45 ml 0.1 M NaCl (total volume of 50 ml), while mixing the pH is raised to 10.0. The sample is centrifuged for 10 min at 1430 G and the supernatant (test solution 7) is separated from the precipitate. The precipitate remaining in the centrifuge tube is washed by re-suspending in water (total volume of 50 ml) and pH is raised to 12 to dissolve the precipitate (test solution 8).

Figure 5:
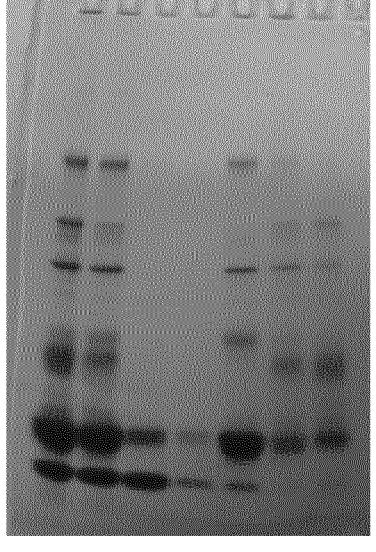

SDS-PAGE is performed on test solutions 3 to 8 as illustrated in FIG. 5.

Dry matter is determined in test solution 7 after dialysis against water to remove salt, silicate and other low molecular weight material using a dialysis tube (Cellulose membrane 14 kD cut off, Sigma-Aldrich, USA cat. no.: D9652).

Silicate test was performed on test solution 7 and 8 FIG. 5:

Lane 1: Casein whey, test solution 2

Lane 2: LF depleted casein whey, test solution 3

Lane 3: Supernatant after precipitation of whey proteins with silicate, test solution 5

Lane 4: Washing fraction, test solution 6

Lane 5: Released proteins from silicate precipitate at pH 10.0, test solution 7

Lane 6: Dissolved silicate from protein precipitation, test solution 8

Lane 7: Dissolved silicate from LF precipitation, test solution 4

The SDS PAGE analysis of FIG. 5, illustrates that in step 1 the sodium metasilicate solution is capable of precipitating LF (see lane 2), where practically all the LF is removed. The LF product contains LF and a small amount of the other whey proteins, see lane 7. In step 2 all the proteins present in the LF depleted casein whey except alpha-la are precipitated with sodium metasilicate—see lane 3 which shows that only a very small fraction of the beta-lg and practically all the alpha-la is in test solution 5, resulting in a highly enriched alpha-la product. Further, it is seen that after washing of the precipitate with water practically all the precipitated proteins are released in one pool at pH 10 (see lane 5), resulting in a beta-lg enriched fraction. It is important to note that at pH 10 the major part of the silicate is still precipitated. There is practically no protein left in this precipitate when dissolved at pH 12 (see lane 6) very weak bands are showing.

Dry matter result on dialysed test solution 7 shows that 3.1 mg dry matter is removed per ml casein whey.

The concentration of silicate in the released protein product at pH 10 (test solution 7) is more than 10 times lower than in test solution 8 (dissolved silicate precipitate) meaning that less than 10% of the applied water glass is recovered in the protein product.

The dissolved precipitate, test solution 8 can be used in another cycle to precipitate whey proteins in casein whey.

Example 6. Isolating Whey Proteins from Microfiltrated Whey (Native Whey from Microfiltration of Milk) Using Silicate 200 ml of microfiltrated whey (test solution 4) is mixed with 2 ml of water glass at 25° C. pH is adjusted to a final pH value of 6.0 with 1 M HCl solution. Following incubation for 60 minutes with stirring at ambient temperature the sample is centrifuged for 10 min at 1430 G and the supernatant (test solution 5) is separated from the precipitate.

The precipitate remaining in the centrifuge tube is washed by re-suspending in 190 ml water (total volume of 200 ml) and then centrifuged again, the supernatant is removed (test solution 6).

The proteins are released from the precipitate by adding 50 ml 0.1 M NaCl, while mixing the pH is raised to 10.0. The sample is centrifuged for 10 min at 1430 G and the supernatant (test solution 7) is separated from the precipitate, this step is repeated and the supernatant is pooled with test solution 7. The precipitate remaining in the centrifuge tube is dissolved by re-suspending in water (total volume of 200 ml) and pH is raised to 12 (test solution 8).

Figure 6:
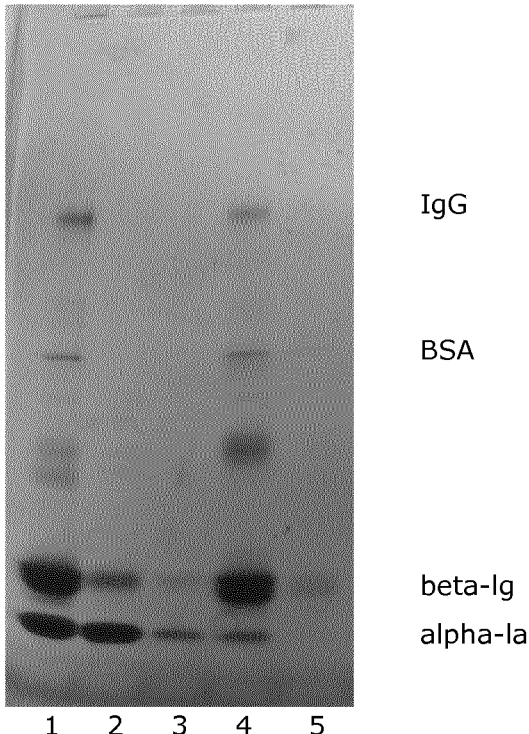

SDS-PAGE is performed on test solutions 4 to 8 as illustrated in FIG. 6.

Dry matter is determined in test solution 7 after dialysis against water to remove salt, silicate and other low molecular weight material using a dialysis tube (Cellulose membrane 14 kD cut off, Sigma-Aldrich, USA cat. no.: D9652).

Silicate test was performed on test solution 7 and 8

FIG. 6:
   Lane 1: Micro filtrated whey, test solution 4
   Lane 2: Supernatant after precipitation of whey proteins with silicate, test solution 5
   Lane 3: Washing fraction, test solution 6
   Lane 4: Released proteins from silicate precipitate at pH 10.0, test solution 7
   Lane 5: Dissolved silicate precipitate, test solution 8.

The SDS PAGE analysis of FIG. 6, illustrates that the sodium metasilicate solution is precipitating all the proteins present in the micro filtered whey except alpha-la—see lane 2 which shows that only a very small fraction of the beta-lg and practically all the alpha-la is in test solution 5, resulting in a highly enriched alpha-la product. Further, it is seen that after washing of the precipitate with water practically all the precipitated proteins are released in one pool at pH 10 (see lane 4), resulting in a beta-lg enriched fraction. It is important to note that at pH 10 the major part of the silicate is still precipitated. There is practically no protein left in this precipitate when dissolved at pH 12 (see lane 5) very weak bands are showing.

The concentration of silicate in the released protein product at pH 10 (test solution 7) is more than 10 times lower than in test solution 8 (dissolved silicate precipitate) meaning that less than 10% of the applied water glass is recovered in the protein product.

The dissolved precipitate, test solution 8 can be used in another cycle to precipitate whey proteins in micro-filtered whey.

Example 7. Isolating Whey Proteins from Sweet Whey Using Different Concentrations of Silicate 60 ml of sweet whey (test solution 4) is divided into 6 samples (A through F respectively) of 10 ml whey, different amounts of waterglass are added. A: 666 µl, B: 333 µl, C: 200 µl, D: 143 µl E: 111 µl, F: 83 µl. pH was adjusted in all solutions to 6.0 with 1 M HCl. Following incubation for 60 minutes with stirring at ambient temperature the samples are centrifuged for 10 min at 1430 G and the supernatants (test solutions 4-9) separated from the precipitates. SDS-PAGE is performed on test solution 2-8 as illustrated in FIGS. 7A and 7B.

Figure 7A:
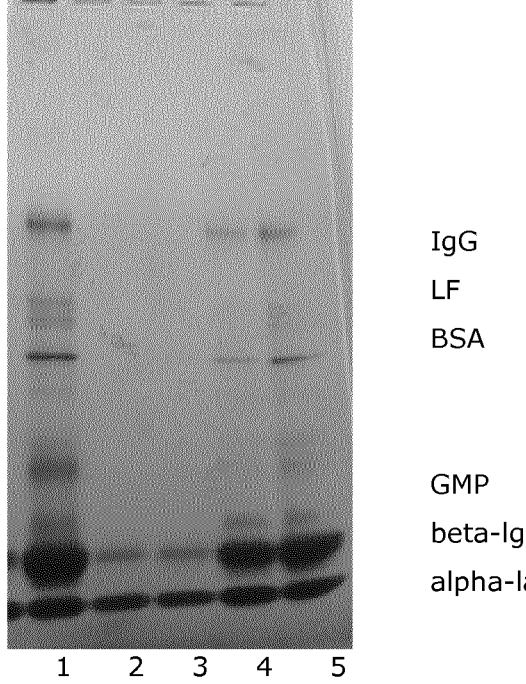
Figure 7B:
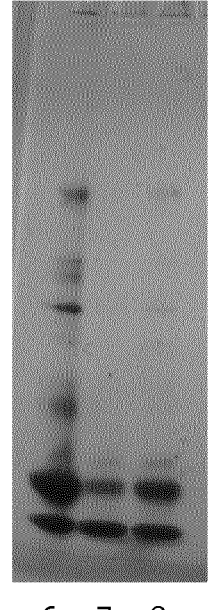

FIG. 7A:
   Lane 1: Test solution 3, sweet whey
   Lane 2: Test solution 4, supernatant from 666 µl water-glass per 10 ml sweet whey
   Lane 3: Test solution 5, supernatant from 333 µl water-glass per 10 ml sweet whey
   Lane 4: Test solution 8, supernatant from 111 µl water-glass per 10 ml sweet whey
   Lane 5: Test solution 9, supernatant from 83 µl waterglass per 10 ml sweet whey FIG. 7B:
   Lane 6: Test solution 3, sweet whey
   Lane 7: Test solution 6, supernatant from 200 µl water-glass per 10 ml sweet whey
   Lane 8: Test solution 7, supernatant from 143 µl water-glass per 10 ml sweet whey The SDS PAGE analysis of FIGS. 7A and 7B, illustrates that the sodium metasilicate solution is capable of precipitating the major part of the proteins present in the sweet whey—see lane 2, 3 and 7, though there is still a fraction of the alpha-la left in the supernatants. When the concentration of water glass is decreased especially the alpha-la concentration in the supernatant is increased, for 200, 143, 111 and 83 µm water glass per 10 ml whey no alpha-la precipitates, the intensity of the alpha-la band is the same as for the sweet whey (see lane 4, 5, 7 and 8 compared with lane 1 and 6). With a decrease of water glass concentration also more beta-lg and other whey proteins appear in the supernatants (see lane 4, 5 and 8). Test solution 6 (see lane 7) contains alpha-la and a minor fraction of beta-lg, there is no BSA, LF or immunoglobulin present, resulting in a highly enriched alpha-la product.

Glycomacropeptide (GMP, weak band right above the beta-lg on the SDS-PAGE) is precipitated together with the metasilicate for 666 µl and 333 µl waterglass/10 ml whey (see lane 2 and 3) resulting in a very pure alpha-la product. For 200 µl waterglass per 10 ml sweet whey a fraction of the GMP is still in solution together with the highly enriched alpha-la product (see lane 7).

Example 8. Isolating Whey Proteins from Sweet Whey Using Silicate 15 ml of sweet whey (test solution 3) is mixed with 0.3 ml of waterglass at 25° C. pH is adjusted to a final pH value of 6.0 with 1 M HCl solution. Following incubation for 60 minutes with stirring at ambient temperature the sample is centrifuged for 10 min at 1430 G and the supernatant (test solution 4) is separated from the precipitate.

The precipitate remaining in the centrifuge tube is washed by re-suspending in 10 ml water and then centrifuged again.

The proteins are released from the precipitate by adding 15 ml 0.1 M NaCl, while mixing the pH is raised to respectively 8.0, 9.0 and 10.0, at pH 8.0 and 9.0 a 250 µl sample is taken out and centrifuged at 1430 G for 10 min (test solution 5 and 6). The sample at pH 10.0 is centrifuged for 10 min at 1430 G and the supernatant (test solution 7) is separated from the precipitate.

14 ml of water is added to the precipitate and pH is increased to 11 while mixing to dissolve the silicate, test solution 8.

Figure 8:
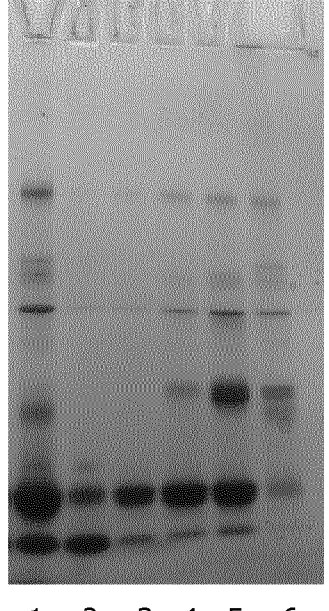

SDS-PAGE is performed on test solutions 2 to 8 as illustrated in FIG. 8.

Test solution 7 is dialysed against water to remove salt, silicate and other low molecular weight material, using a dialysis tube (Cellulose membrane 14 kD cut off, Sigma-Aldrich, USA cat. no.: D9652). The dry matter of the dialysed test solution 7 was determined.

FIG. 8:
   Lane 1: Sweet whey, test solution 3
   Lane 2: Supernatant after silicate precipitation, test solution 4
   Lane 3: Supernatant pH 8.0, test solution 5
   Lane 4: Supernatant pH 9.0, test solution 6
   Lane 5: Supernatant pH 10.0, test solution 7
   Lane 6: Dissolved silicate precipitate, test solution 8

The SDS PAGE analysis of FIG. 8, illustrates that the sodium metasilicate solution is capable of precipitating the major part of the proteins present in the sweet whey except the alpha-la, GMP and a small fraction of beta-lg—see lane 2 resulting highly enriched alpha-la product.

The proteins precipitated together with the silicate are released by increasing pH, the higher pH the more protein is released. Elution at pH 8 a rather pure beta-lg product is produced (see lane 3), at pH 9 the beta-lg and a fraction of IgG and BSA are released (see lane 4), at pH 10 the major part of the proteins is released (see lane 5). When the water glass is dissolved only a minor fraction of protein especially the LF is released resulting in a LF enriched fraction (see lane 6).

Silicate test shows that the concentration of silicate in test solution 7 (fractions with released protein pH 10) is more than 10 times lower than in test solution 8 (dissolved silicate precipitate) meaning that more than 90% of the applied silicate is recovered in a separate fraction and can be re-used in another cycle to precipitate whey proteins in sweet whey.

Dry matter result on dialysed test solution 7 shows that 3.3 mg dry matter is removed per ml sweet whey.

Example 9A. Isolating Whey Proteins from Casein Whey and Demineralized Casein Whey Using Silicate 30 ml of casein whey (test solution 2) is divided into 3 10 ml samples (sample A through C respectively), 39 ml of demineralized concentrated whey (test solution 7) is divided into 3 13 ml samples (sample D through F respectively). Sample A and D are mixed with 0.2 ml of waterglass at 50° C., sample B and E are mixed with 0.133 ml of waterglass at 50° C. and sample C and F are mixed with 0.1 ml of waterglass at 50° C. pH is adjusted in all samples to a final pH value of 5.6 with 1 M HCl solution. Following incubation for 30 minutes with stirring at 50° C. the sample is centrifuged for 10 min at 1430 G and the supernatants are collected (A-C: test solutions 3 to 5, D-F: test solutions 8 to 10). SDS-PAGE is performed on test solutions 2 to 5 and 7-10 as illustrated in FIGS. 9A and 9B.

Figure 9A:
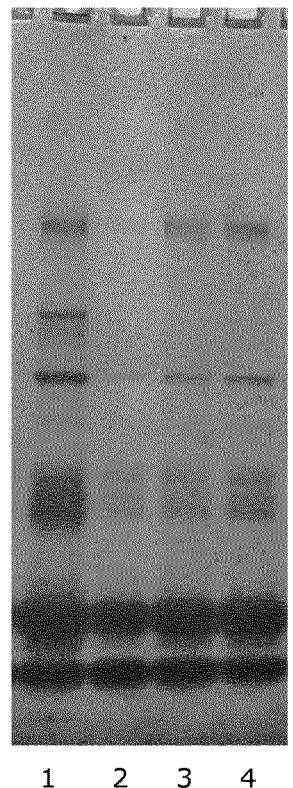
Figure 9B:
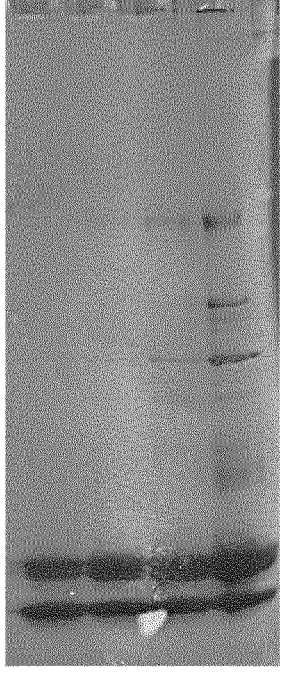

FIG. 9A:
Lane 1: Casein whey, test solution 2
Lane 2: Supernatant, 0.2 ml waterglass per 10 ml whey, test solution 3
Lane 3: Supernatant, 0.133 ml waterglass per 10 ml whey, test solution 4
Lane 4: Supernatant, 0.1 ml waterglass per 10 ml whey, test solution 5
FIG. 9B:
Lane 5: Supernatant, 0.2 ml waterglass per 13 ml demineralised casein whey, test solution 8
Lane 6: Supernatant, 0.133 ml waterglass per 13 ml demineralized casein whey, test solution
Lane 7: Supernatant, 0.1 ml waterglass per 13 ml demineralised casein whey, test solution
Lane 8: Demineralised casein whey, test solution 7
The SDS PAGE analysis of FIGS. 9A and 9B, illustrates that the sodium metasilicate solution in the tested concentrations is capable of precipitating more protein from the demineralised casein whey (test solution 7) than the casein whey (test solution 2). Practically all IgG, LF and BSA is precipitated for all three metasilicate concentrations for the demineralized casein whey, see lane 5-7 (very faint bands for BSA and IgG are detected in lane 7). For casein whey both 0.133 and 0.1 ml waterglass per 10 ml whey, a fraction of IgG and BSA is still in solution (see lane 3 and 4).

0.2 and 0.133 ml waterglass per 13 ml demineralized whey results in highly enriched alpha-la products (see lane 5).

Example 9B. Isolating Whey Proteins from Concentrated Casein Whey and Demineralized Concentrated Casein Whey Using Silicate 45 ml of concentrated casein whey (test solution 5) is divided into 3 15 ml samples (sample A through C respectively), 46.8 ml of demineralized concentrated whey (test solution 6) is divided into 3 15.6 ml samples (sample D through F respectively). Sample A and D are mixed with 0.375 ml of waterglass at 25° C., sample B and E are mixed with 0.250 ml of waterglass at 25° C. and sample C and F are mixed with 0.188 ml of waterglass at 25° C. pH is adjusted in all samples to a final pH value of 5.75 with 1 M HCl solution. Following incubation for 120 minutes with stirring at ambient temperature the samples are centrifuged for 10 min at 1430 G and the supernatants are collected (A-C: test solutions 10 to 12, D-F: test solutions 7 to 9). SDS-PAGE is performed on test solutions 5 to 12 as illustrated in FIG. 9C.

Figure 9C:
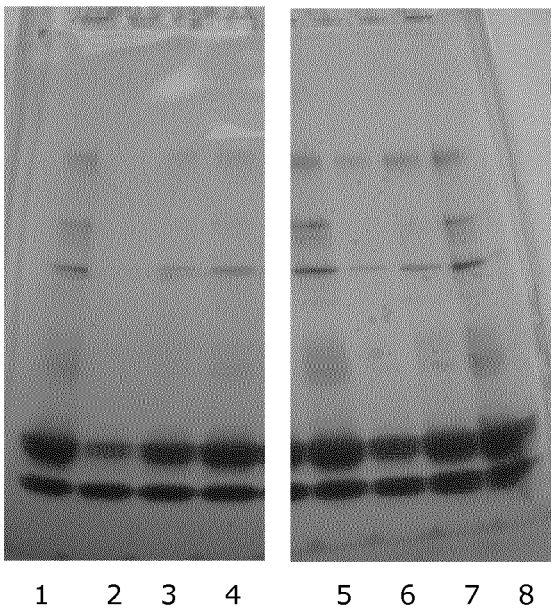

FIG. 9C:
Lane 1: Demineralised concentrated casein whey, test solution 6
Lane 2: Supernatant from D after silicate precipitation (0.375 ml), test solution 10
Lane 3: Supernatant from E after silicate precipitation (0.250 ml), test solution 11
Lane 4: Supernatant from F after silicate precipitation (0.188 ml), test solution 12
Lane 5: Concentrated casein whey, test solution 5
Lane 6: Supernatant from A after silicate precipitation (0.375 ml), test solution 7
Lane 7: Supernatant from B after silicate precipitation (0.250 ml), test solution 8
Lane 8: Supernatant from C after silicate precipitation (0.188 ml), test solution 9
The SDS PAGE analysis of FIG. 9C, illustrates that the sodium metasilicate solution (0.375 ml waterglass per 15.6 ml demineralized concentrated casein whey) is capable of precipitating all the proteins present in the demineralized concentrated casein whey except alpha-la—see lane 2, it shows that only a very small fraction of the beta-lg and practically all the alpha-la is in test solution 10, resulting in a highly enriched alpha-la product. With lower concentration of silicate (0.250 ml waterglass per 15.6 ml demineralized concentrated casein whey) practically all the IgG and BSA is precipitated (see lane 3, only faint bands are detected) more beta-lg is recovered in the alpha-la product.

For the non-demineralised concentrated whey less protein is precipitated for the different concentrations of silicate tested compared to the demineralized whey (see lane 6 compared with lane 2), for 0.375 ml waterglass per 15 ml of concentrated casein whey faint bands of IgG and BSA can be detected (see lane 6) and a significant amount of beta-lg is still left in the alpha-la product compared to the experiment with the demineralized concentrated whey.

Example 10. Release of Whey Proteins from Silicate/Protein Precipitate

60 L of casein whey (test solution 2) is mixed with 1200 ml of waterglass at 25° C. pH is adjusted to a final pH value of 5.8 with 1 M HCl solution. Following incubation for 60 minutes with stirring at ambient temperature the solution is passed through a decanter centrifuge (3500 G, MD80 from Lemitec, Germany) to separate the precipitate from the solution. The precipitate (7.12 kg) is collected and washed with water. 21 L of water is mixed with the precipitate and the solution is passed through the decanter centrifuge one more time. The washed silicate/protein precipitate is collected.

170 g of precipitate is divided into 17 samples of 10 g (Sample 1 through 17). Each 10 g sample is added 30 ml of buffer and pH is adjusted with 1 M NaOH. Table 1 shows the nature of the buffer and specific pH-value for each sample. The procedure was performed at ambient temperature.

After pH adjustment each sample is centrifuged for 10 min at 1430 G and the supernatants (test solution 1-17) are separated from the precipitates. The test solutions are measured on a spectrophotometer (Biobase, BK-UV1800, China) at 280 and 310 nm and 280-310 nm is calculated, see table 2.

TABLE 1

| Sample ID | Buffer | pH adjustment |
|---|---|---|
| 1, reference | Water | 12.5 |
| 2 | Water | 8.5 |
| 3 | Water | 9.5 |
| 4 | Water | 10 |
| 5 | Water | 10.5 |
| 6 | 0.1M NaCl | 8.5 |
| 7 | 0.1M NaCl | 9.5 |
| 8 | 0.1M NaCl | 10 |
| 9 | 0.1M NaCl | 10.5 |
| 10 | 0.25M NaCl | 8.5 |
| 11 | 0.25M NaCl | 9.5 |
| 12 | 0.25M NaCl | 10 |
| 13 | 0.25M NaCl | 10.5 |
| 14 | 0.5M NaCl | 8.5 |
| 15 | 0.5M NaCl | 9.5 |
| 16 | 0.5M NaCl | 10 |
| 17 | 0.5M NaCl | 10.5 |

TABLE 2

| Solution # | Buffer | pH adjustment | OD 280-310 nm |
|---|---|---|---|
| 1, reference | Water | 12.5 | 16.0 |
| 2 | Water | 8.5 | 4.34 |
| 3 | Water | 9.5 | 6.9 |
| 4 | Water | 10 | 9.42 |
| 5 | Water | 10.5 | 11.58 |
| 6 | 0.1M NaCl | 8.5 | 4.52 |
| 7 | 0.1M NaCl | 9.5 | 9.16 |
| 8 | 0.1M NaCl | 10 | 11.48 |
| 9 | 0.1M NaCl | 10.5 | 12.5 |
| 10 | 0.25M NaCl | 8.5 | 4.64 |
| 11 | 0.25M NaCl | 9.5 | 9.3 |
| 12 | 0.25M NaCl | 10 | 10.88 |
| 13 | 0.25M NaCl | 10.5 | 12.08 |
| 14 | 0.5M NaCl | 8.5 | 5.56 |
| 15 | 0.5M NaCl | 9.5 | 10.16 |
| 16 | 0.5M NaCl | 10 | 11.6 |
| 17 | 0.5M NaCl | 10.5 | 12.84 |

The spectrophotometric analysis of table 2, illustrates that for all buffers used to separate the proteins from the silicate, the higher pH the more protein is released when comparing to a sample where the silicate is totally dissolved (reference, 280-310 nm=16.0

More protein is released with 0.1 M NaCl as buffer than using water as the buffer.

Example 11. Release of Whey Proteins from Silicate/Protein Precipitate at Elevated Temperatures 50 g of precipitate (produced as described in example 10) is divided into 5 samples of 10 g (Sample 1 through 5). Each 10 g sample is added 30 ml of 0.1 M NaCl and pH is adjusted to 9.5 with 1 M NaOH. Sample 1 is heated to 30° C. on a water bath, sample 2 is heated to 37° C., sample 3 is heated to 40° C. on a water bath, sample 4 is heated to 45° C. and sample 5 is heated to 50° C.

Each sample is centrifuged for 10 min at 1430 G and the supernatants (test solution 1-5) are separated from the precipitate. The test solutions are measured on a spectrophotometer (Biobase, BK-UV1800, China) at 280 and 310 nm and 280-310 nm is calculated, see table 3.

TABLE 3

| Solution # | Temperature, ° C. | OD 280-310 nm |
|---|---|---|
| Reference | — | 16.0 |
| 1 | 30 | 10.5 |
| 2 | 37 | 12.3 |
| 3 | 40 | 13.0 |
| 4 | 45 | 14.4 |
| 5 | 50 | 14.82 |

The spectrophotometric analysis of table 3, illustrates that the higher temperature used during the separation of proteins from silicate the more protein is released. 65.6% of the protein is released at 30° C. this is increased to 92.6% when the temperature is raised to 50° C.

Example 12. Release of Whey Proteins from Silicate/Protein Precipitate at 30° C. Over Time at pH 9.5

60 g of precipitate (produced as described in example 10) is divided into 6 samples of 10 g (Sample 1 through 6). Each 10 g sample is added 30 ml of 0.1 M NaCl and pH is adjusted to 9.5 with 1 M NaOH. All samples are heated to 30° C. on a water bath. Sample 1 is incubated for 1 min, sample 2 is incubated for 20 min at 30° C., sample 3 is incubated for 30 min at 30° C., sample 4 is incubated for 40 min at 30° C., sample 5 is incubated for 50 min at 30° C. and sample 6 is incubated for 60 min at 30° C.

After incubation each sample is centrifuged for 10 min at 1430 G and the supernatants (test solution 1-6) are separated from the precipitate. The test solutions are measured on a spectrophotometer (Biobase, BK-UV1800, China) at 280 and 310 nm and 280-310 nm is calculated, see table 4.

TABLE 4

| Solution # | Time of inc., min | OD 280-310 nm |
|---|---|---|
| Reference | — | 16.0 |
| 1 | 1 | 10.18 |
| 2 | 20 | 13.08 |
| 3 | 30 | 13.26 |
| 4 | 40 | 13.72 |
| 5 | 50 | 13.88 |
| 6 | 60 | 14.16 |

The spectrophotometric analysis of table 4, illustrates that at 30° C. the longer incubation time the more protein is released from the silicate. At 1 min 63.6% is released this is increased to 88.5% when incubation time is prolonged to 60 min.

Example 13. Release of Whey Proteins from Silicate/Protein Precipitate at 30° C. Over Time at pH 8.5

40 g of precipitate (produced as described in example 10) is divided into 4 samples of 10 g (Sample 1 through 4). Each 10 g sample is added 30 ml of 0.1 M NaCl and pH is adjusted to 8.5 with 1 M NaOH. All samples are heated to 30° C. on a water bath. Sample 1 is incubated for 1 min, sample 2 is incubated for 20 min at 30° C., sample 3 is incubated for 40 min at 30° C. and sample 4 is incubated for 60 min at 30° C.

After incubation each sample is centrifuged for 10 min at 1430 G and the supernatants (test solution 1-4) are separated from the precipitate. The test solutions are measured on a spectrophotometer (Biobase, BK-UV1800, China) at 280 and 310 nm and 280-310 nm is calculated, see table 5.

TABLE 5

| Solution # | Time of inc., min | OD 280-310 nm |
| --- | --- | --- |
| Reference | — | 16.0 |
| 1 | 1 | 7.6 |
| 2 | 20 | 9.12 |
| 3 | 40 | 9.46 |
| 4 | 60 | 10.28 |

The spectrophotometric analysis of table 5, illustrates that if pH is 8.5 at 30° C. it takes more time to release the protein than at pH 9.5 (see example 12) at 1 min 47.5% of the protein is released at 60 min 64.3% of the protein is released (88.5% for pH 9.5 after 60 min of incubation at 30° C.).

Example 14. Release of Whey Proteins from Silicate/Protein Precipitate, Re-Use of the Silicate 30 g of precipitate (produced as described in example 10) is added 90 ml of 0.1 M NaCl and pH is adjusted to 9.5 with 1 M NaOH. The sample is heated to 50° C. on a water bath.

The sample is centrifuged for 10 min at 1430 G and the supernatant is separated from the precipitate.

Another 90 ml of 0.1 M NaCl is added to the precipitate and pH is adjusted to 9.5 with 1 M NaOH. The sample is heated to 50° C. on a water bath. The sample is centrifuged for 10 min at 1430 G and the supernatant is separated from the precipitate.

The precipitate is added 5 M NaOH until it is totally dissolved (pH 12). The silicate solution is used for precipitation of proteins from casein whey:

40 ml of casein whey (test solution 2) is divided into 4 samples (A through D respectively) of 10 ml. Silicate solution pH 12 as described above is added to each sample: A: 2 ml silicate solution, B: 1 ml silicate solution, C: 0.67 ml and D: 0.5 ml pH is adjusted with 1 M HCl in all samples to 5.8. Following incubation for 60 minutes with stirring at ambient temperature the samples are centrifuged for 10 min at 1430 G and the supernatant (test solutions 3-6) separated from the precipitate.

Figure 10:
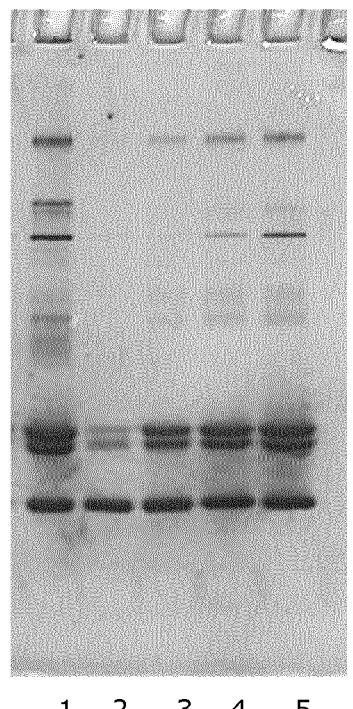

SDS-PAGE is performed on test solution 2-6 as illustrated in FIG. 10.

FIG. 10:

Lane 1: Casein whey, test solution 2

Lane 2: Supernatant, 2 ml silicate solution per 10 ml whey, test solution 3

Lane 3: Supernatant, 1 ml silicate solution per 10 ml whey, test solution 4

Lane 4: Supernatant, 0.67 ml silicate solution per 10 ml whey, test solution 5

Lane 5: Supernatant, 0.5 ml silicate solution per 10 ml whey, test solution 6

The SDS PAGE analysis of FIG. 10, illustrates that the dissolved sodium metasilicate solution can be re-used to precipitate the major part of the proteins present in the casein whey except the alpha-la. With 2 ml of silicate solution per 10 ml casein whey IgG, LF, BSA and the major part of the beta-lg are precipitated (see lane 2) resulting in a highly enriched alpha-la supernatant. With 1 ml of silicate solution per 10 ml casein whey most of the IgG, LF, BSA and part of the beta-lg are precipitated (see lane 3) resulting in an enriched alpha-la supernatant.

In general, when the concentration of dissolved silicate solution is decreased more protein is present together with the alpha-la in the supernatant (see lane 3, 4 and 5)

Example 15. Larger Scale Production of an Alpha-La Enriched Fraction and a Beta-lg Enriched Fraction from Casein Whey with Silicate 50 L of skim milk (from local supermarket) is heated through a heat exchanger to 35° C. pH is adjusted to pH 4.5 with 1 M HCl. The major part of the precipitated casein is removed by passing the milk through an 80 μm nylon filternet. The resulting whey (40 L) is passed a decanter centrifuge (3500 G, MD80 from Lemitec, Germany) to remove fines (test solution A).

The beta-lg is precipitated together with the IgG, LF and BSA with metasilicate: 38 L of test solution A is added 760 ml waterglass pH is adjusted to 5.8 and the temperature is 28° C.

Following incubation for 60 minutes with stirring the solution is passed through the decanter (3500 G) to separate the precipitate from the casein whey. The clarified liquid from the decanter is a highly alpha-enriched solution (test solution B).

Test solution B is passed through a 1 μm filter cartridge (Vyair, UK: 10" PP Sediment filter) to clear the solution before ultrafiltration (test solution C). Test solution C, 33.3 L are concentrated on a 10 kD hollow fiber membrane to 1.5 L. The retentate is then diafiltrated with 5 times 3 L of water. The diafiltrated retentate, 1.3 L (test solution D) is ready for drying.

The protein/metasilicate precipitate (The solids from the decanter=3.64 kg) is washed: 15 L of water is added to the precipitate, after mixing the solution is passed through the decanter (3500 G), resulting in 3.24 kg of solids. The clarified liquid phase from the decanter is the wash fraction (test solution E)

The proteins are released from the precipitate by adding 9.5 L of 0.1 M NaCl pH is adjusted to 9.5 and the temperature raised to 30° C. Incubation for 1 hr. The solution is passed through the decanter (3500 G). The clarified liquid phase from the decanter (test solution F) containing the released proteins is pH-adjusted to 7.5 with 1 M HCl.

The solids from the decanter, 2.82 kg is added another 8.5 L of 0.1 M NaCl and pH is adjusted to 9.5 and the temperature raised to 30° C. Incubation for 10 min. The solution is passed through the decanter (3500 G). The liquid phase (test solution G) from the decanter containing released proteins is pH-adjusted to 7.5 with 1 M HCl.

Test solution F and G are pooled containing a highly enriched beta-lg fraction, 16.7 L. The fraction is concentrated on a 10 kD hollow fiber membrane to 1.5 L. The retentate is diafiltrated with 5 times 3 L of water. The final product volume is 1.9 L (test solution H) is ready for drying.

Dry matter determination is performed on test solution D and H. The protein content is determined on alpha-la enriched product (a fraction of test solution D is freeze dried before testing) with elementary analysis: Determination of nitrogen content. SDS-PAGE is performed on test solution A, B, C, E, F and G as illustrated in FIGS. 11A and 11B.

Figure 11A:
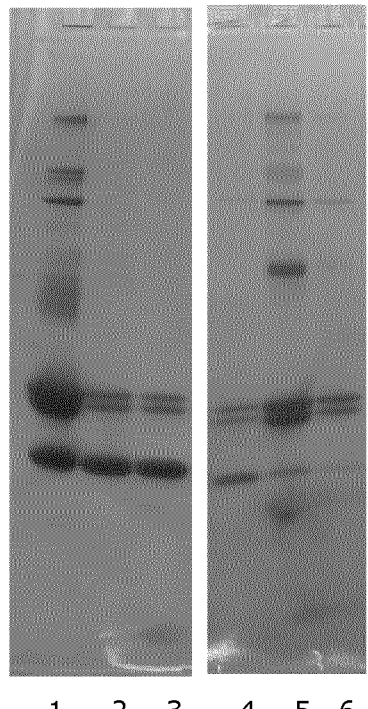
Figure 11B:
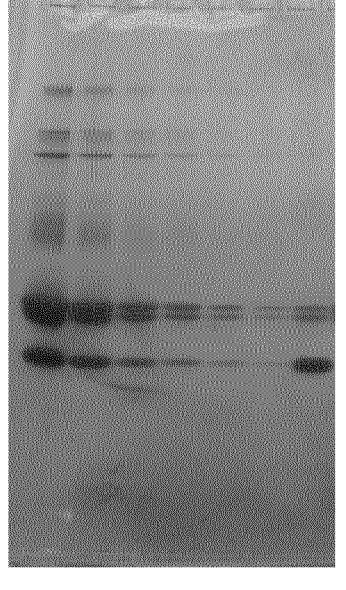

FIG. 11A:
Lane 1: Casein whey, test solution A
Lane 2: alpha-la enriched product, test solution B
Lane 3: alpha-la enriched product after 1 μm filter cartridge, test solution C
Lane 4: Wash fraction of protein/silicate precipitate, test solution E
Lane 5: beta-lg enriched fraction, release of protein from silicate precipitate (1), test solution F
Lane 6: beta-lg enriched fraction, release of protein from silicate precipitate (2), test solution G FIG. 11B:
Lane 7: Casein whey, test solution 2
Lane 8: Casein whey diluted 2 times, test solution 2
Lane 9: Casein whey diluted 4 times, test solution 2
Lane 10: Casein whey diluted 8 times, test solution 2
Lane 11: Casein whey diluted 16 times, test solution 2
Lane 12: Casein whey diluted 32 times, test solution 2
Lane 13: alpha-la enriched product after 1 μm filter cartridge, test solution C The SDS PAGE analysis of FIG. 11B (lane 13), illustrates that a highly enriched alpha-la product is produced. It is estimated from the SDS-PAGE that approximately 90% of the beta-lg is removed from the casein whey. Assumed the casein whey contains 3.3 g/L beta-lg and 1.2 g/L alpha-la and 95% of the alpha-la is recovered in test solution C the purity of the alpha-la is 77.6% (0.95×1.2)/((0.95×1.2)+(0.1× 3.3)).

The dry matter of test solution D is determined to be 2.68%. With 1.3 L of product it results in 34.8 g of product from 33.3 L of beta-lg depleted casein whey.

The nitrogen content was determined on a freeze dried sample of test solution D. The nitrogen content was 14.32% this results in a protein content of 14.32%×6.25=89.5%. The moisture of the freeze dried sample was determined to be 4.49%. Based on dry matter, the protein content is calculated to be 93.7%.

The wash fraction (test solution E) contains a minor fraction of the alpha-la (see lane 4) and can be returned to the liquid phase from the decanter (test solution B) to increase the yield of alpha-la product.

Test solution F (see lane 5) contains the major fraction of beta-lg, BSA, LF and IgG released from the metasilicate/ protein precipitate. Test solution G (see lane 6) contains a small amount of mainly beta-lg.

The dry matter content of the concentrated and diafiltrated beta-lg product was determined to be 6.35%. With 1.9 L of product it results in 120.65 g from 40 L of casein whey.

The remaining metasilicate precipitate (2.16 kg, dry matter content=9.37%) was adjusted to pH 12.2 by adding 5 M NaOH. The content of protein was very low (tested with SDS-PAGE, data not shown). The dissolved silicate can be reused in another process cycle.

Example 16. Production of an Alpha-La Enriched Fraction and a Beta-lg Enriched Fraction from Casein Whey with Silicate and Microfiltration 850 ml of casein whey (test solution 2) is mixed with 17 ml of waterglass at a temperature of 40-45° C., pH is adjusted with 1 M HCl to 5.8 whereby a substantial precipitate is formed. The solution with the suspended precipitate is incubated for 1 hr with stirring.

After incubation the solution with the suspended precipitate is microfiltrated on a 0.2 micro meter hollow fiber membrane (Spectrum Labs, USA cat. no.: 502-P20U-10-N, 470 cm2). When 400 ml of permeate is collected (alpha-la enriched solution, test solution 3) 1 L of 0.1 M NaCl is added to the retentate (=wash of retentate to remove the alpha-la enriched solution from the precipitate). When another 1450 ml of permeate is removed (alpha-la enriched solution, test solution 4), 200 ml of 0.1 M NaCl is added to the 300 ml retentate (viscous suspension of the precipitate). While re-circulating the permeate into the retentate the pH is adjusted to 9.5 with 1 M NaOH, temperature is 30° C., the system recirculates for 20 min (the proteins are gradually released from the precipitated silicate). After 20 min of recirculation 200 ml of permeate is collected=released protein from the silicate precipitate (beta-lg enriched fraction, test solution 5)

Another 4 times of 200 ml 0.1 M NaCl is added to the retentate and the permeate is collected in 4, 200 ml fractions (test solution 6 to 9).

400 ml of water is finally added to the retentate, the permeate is recirculated and the pH is adjusted to 12.2 with 5 M NaOH to dissolve the silicate. 400 ml of permeate is then collected as the dissolved silicate solution (test solution 10).

Figure 12:
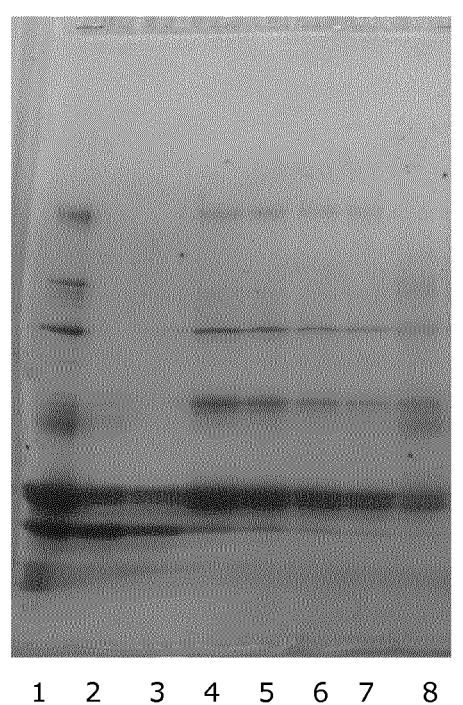

SDS-PAGE is performed on test solution 2-10 as illustrated in FIG. 12.

FIG. 12
Lane 1: Casein whey, test solution 2
Lane 2: Alpha-la enriched permeate, 400 ml, test solution 3
Lane 3: Alpha-la enriched permeate, 1450 ml, test solution 4
Lane 4: Permeate, released protein from silicate precipitate, fraction 1, 200 ml, test solution 5
Lane 5: Permeate, released protein from silicate precipitate, fraction 2, 200 ml, test solution 6
Lane 6: Permeate, released protein from silicate precipitate, fraction 3, 200 ml, test solution 7
Lane 7: Permeate, released protein from silicate precipitate, fraction 4, 200 ml, test solution 8
Lane 8: Permeate, 400 ml pH 12.2, test solution 10

The SDS PAGE analysis of FIG. 12, illustrates that test solution 3 and 4 contain a highly enriched alpha-la product containing mainly alpha-la, while a major part of the beta-lg is precipitated with the silicate together with practically all the BSA, LF and IgG (see lane 2 and 3), the fractions are totally clear and can be pooled and ultrafiltrated on a 10 kD membrane and dried.

Test solution 6 to 9 (test solution 9 is not shown on the SDS-PAGE) are permeates containing proteins released from the silicate precipitate (the retentate). The fractions are totally clear solutions containing beta-lg, BSA and IgG and a minor fraction of the alpha-la. The fractions can be pooled and ultrafiltrated on a 10 kD membrane and dried.

Test solution 10, which is the dissolved silicate only contains a small fraction of the protein (see lane 8) compared to the casein whey (see lane 1).

The invention claimed is:
1. A method for isolating one or more proteins naturally occurring in mammalian milk from an aqueous protein solution comprising said one or more proteins and impurities and being selected from the group consisting of milk and whey and concentrates and derivatives thereof, the method comprising:

A. providing an aqueous solution containing the one or more proteins and the impurities, wherein said aqueous solution is selected from the group consisting of milk and whey and concentrates and derivatives thereof, B. adding a water-soluble silicate to the solution of step (A) such that the total concentration of silicon in the form of free or complexed silicates in the solution is in the range of 1-750 mM, C. if necessary, adjusting the pH of the resulting solution to a pH in the range of pH 1 to pH 11, D. allowing the silicate to form an insoluble precipitate of a silicate-protein complex, E. separating the silicate-protein complex from the solution as a wet precipitate; and F. dissociating the one or more proteins from the silicate-protein complex, thereby obtaining the isolated protein product.

2. The method according to claim 1 further comprising a step of clarification to remove insoluble and/or colloid particles prior to step B).

3. The method according to claim 1, wherein the separation of the one or more proteins from the silicate-protein complex is done by adjusting the pH of the wet precipitate to a pH in the range of pH 6 to pH 13, such that the one or more proteins are released into solution from the wet precipitate while at least 50% of the silicate from the protein-silicate complex remains in the form of an insoluble precipitate.

4. The method according to claim 1, wherein the separation of the one or more proteins from the silicate-protein complex is done by adjusting pH to below pH 5.0 such that the one or more proteins are released into solution from the wet precipitate while at least 50% of the silicate from the protein-silicate complex remains in the form of an insoluble precipitate.

5. The method according to claim 1, wherein the separation of the one or more proteins from the silicate-protein complex is done by first adjusting the pH of the wet precipitate to a pH in the range of pH 9 to pH 13 to solubilize the silicate-protein complex followed by allowing the silicate to be separated from the silicate-protein complex by a method selected from the group consisting of membrane filtration, selective silicate precipitation with metal ions, selective precipitation of the protein with organic solvents, polymers or lyotropic salts, and adsorption chromatography.

6. The method according to claim 1, wherein the pH of the solution in step C. is adjusted to a pH in the range 2-11.

7. The method according to claim 1, wherein the one or more proteins are selected from the group consisting of alpha-lactalbumin, beta-lactoglobulin, lactoferrin, and lactoperoxidase.

8. The method according to claim 1, wherein the one or more proteins are selected from the group consisting of osteopontin, angiogenin, immunoglobulin G, immunoglobulin A, plasminogen, whey acidic protein (WAP), alkaline phosphatase, acid phosphatase, xanthin oxi-doreductase, catalase, and albumin.

9. The method according to claim 1, wherein the one or more proteins are selected from the group consisting of caseins and casein peptides.

10. The method according to claim 1, wherein the one or more proteins are growth factors.

11. The method according to claim 1, wherein the aqueous solution containing the one or more proteins and the impurities is selected from the group consisting of sweet whey, acid whey, native whey from microfiltration of milk, salty whey from brined cheeses and concentrates and other derivatives hereof.

12. The method according to claim 1, wherein said one or more proteins are one or more first proteins, and said impurities comprise one or more second proteins, such that the method provides the separated one or more first proteins and said one or more second proteins in two different fractions.

13. The method according to claim 12 wherein said one or more first proteins comprise beta-lactoglobulin and said one or more second proteins comprise alpha-lactalbumin, such that the method provides beta-lactoglobulin and alpha-lactalbumin in two different fractions.

14. The method according to claim 13 wherein the alpha-lactalbumin fraction contains less than 50% beta-lactoglobulin relative to alpha-lactalbumin on a dry matter basis.

15. The method according to claim 13 wherein the beta-lactoglobulin fraction contains less than 10% alpha-lactalbumin relative to beta-lactoglobulin on a dry matter basis.

16. The method according to claim 1, further comprising the step of washing the silicate-protein complex to further remove said impurities from the silicate-protein complex, prior to step F.

17. The method according to claim 1, wherein the wet precipitate is a wet cake or an aqueous suspension of the precipitate.

18. The method according to claim 5, wherein the method of membrane filtration is ultrafiltration using a membrane allowing selective passage of silicate ions.

19. The method according to claim 5, wherein the method of adsorption chromatography is ion exchange.

20. The method according to claim 9, wherein the caseins and casein peptides is glycomacropeptide.

21. The method according to claim 10, wherein said growth factors are selected from the group consisting of insulin-like growth factor I (IGF-I), insulin-like growth factor II (IGF-II), epidermal growth factor (EGF), transforming growth factor beta 1 (TGF-β1), transforming growth factor beta 2 (TGF-β2), basic fibroblast growth factor (bFGF), and platelet-derived growth factor (PDGF).

* * * * *